(12) United States Patent
Luo et al.

(10) Patent No.: US 11,262,336 B2
(45) Date of Patent: Mar. 1, 2022

(54) METHOD AND SYSTEM FOR DETECTING AROMATIC COMPOUNDS

(71) Applicant: Applin Biotech Co. Ltd., Zhenjiang (CN)

(72) Inventors: Yiqi Ruben Luo, Zhejiang (CN); Jichun Han, Zhejiang (CN)

(73) Assignee: APPLIN BIOTECH CO. LTD., Hangzhou (CN)

( * ) Notice: Subject to any disclaimer, the term of this patent is extended or adjusted under 35 U.S.C. 154(b) by 267 days.

(21) Appl. No.: 16/294,843

(22) Filed: Mar. 6, 2019

(65) Prior Publication Data

US 2019/0204279 A1    Jul. 4, 2019

Related U.S. Application Data

(63) Continuation of application No. PCT/CN2018/101114, filed on Aug. 17, 2018.

(51) Int. Cl.
| | |
|---|---|
| *G01N 30/72* | (2006.01) |
| *G01N 30/06* | (2006.01) |
| *G01N 30/86* | (2006.01) |
| *G01N 30/88* | (2006.01) |
| *G01N 33/50* | (2006.01) |
| *G01N 33/74* | (2006.01) |
| *G01N 30/02* | (2006.01) |

(52) U.S. Cl.
CPC ......... *G01N 30/7233* (2013.01); *G01N 30/06* (2013.01); *G01N 30/8679* (2013.01); *G01N 30/88* (2013.01); *G01N 33/50* (2013.01); *G01N 33/743* (2013.01); *G01N 2030/027* (2013.01); *G01N 2030/067* (2013.01); *Y10T 436/212* (2015.01); *Y10T 436/24* (2015.01)

(58) Field of Classification Search
CPC . C07J 1/007; C07J 41/0005; G01N 2030/027; G01N 2030/067; G01N 2030/8813; G01N 2030/884; G01N 2560/00; G01N 30/02; G01N 30/06; G01N 30/72; G01N 30/7233; G01N 30/8679; G01N 30/88; G01N 33/50; G01N 33/74; G01N 33/743; Y10T 436/17; Y10T 436/173845; Y10T 436/174614; Y10T 436/18; Y10T 436/212; Y10T 436/24
USPC .......... 436/63, 106, 110, 111, 112, 119, 140, 436/161, 173; 422/70
See application file for complete search history.

(56) References Cited

U.S. PATENT DOCUMENTS

| | | | | |
|---|---|---|---|---|
| 10,267,775 B2* | 4/2019 | Huang | ................... | G01N 1/405 |
| 2007/0269899 A1* | 11/2007 | Shimbo | .............. | G01N 33/6809 436/89 |
| 2019/0170776 A1* | 6/2019 | Kema | ................ | G01N 33/6812 |

OTHER PUBLICATIONS

Vaiano et al. Analytical and Bioanalytical Chemistry, vol. 406, pp. 3579-3587, 2014.*
Luo et al. Journal of Analytical Toxicology, vol. 43, pp. 331-339, Apr. 5, 2019.*
Luo et al. Journal of Chromatography A, vol. 1597, pp. 109-118, Mar. 14, 2019.*

* cited by examiner

*Primary Examiner* — Maureen Wallenhorst
(74) *Attorney, Agent, or Firm* — Muncy, Geissler, Olds & Lowe, P.C.

(57) ABSTRACT

A method for analyzing aromatic compounds, and a reagent kit for LC-MS analysis of aromatic compounds. The method includes preparing a diazonium reagent, contacting aromatic compounds in a sample with the diazonium reagent to form an analyte; and measuring an amount or ratio of the analyte. The reagent kit includes a diazonium reagent, wherein the diazonium reagent includes (i) a diazonium salt that contains a diazonium ion; (ii) an amine and nitrous acid; and/or (iii) a nitrite and an acid.

13 Claims, 19 Drawing Sheets

METHOD AND SYSTEM FOR DETECTING AROMATIC COMPOUNDS

RELATED APPLICATIONS AND PRIORITY CLAIMS

This application is a continuation of PCT application PCT/CN2018/101114, filed Aug. 17, 2018, which claims priority to Chinese Patent Application No. 201710726075.1, filed Aug. 22, 2017, both of which are incorporated herein by reference.

TECHNICAL FIELD

This application relates to chemical analysis, in particular, methods and systems for detecting aromatic compounds.

BACKGROUND

Equipped with power to resolve molecular structures, liquid chromatography-mass spectrometry (LC-MS) has become one of the mainstream tools for performing quantitative analysis of bioactive materials. The applications of LC-MS in clinical diagnosis are increasingly expanding, especially in quantitative analysis of small-molecule compounds. In clinical detection practice, when a sample is in low quantity or an analyte is in low concentration, high sensitivity is a required feature of effective analytical methods. Particularly, in blood analysis, if the sample is a small volume of blood (1 $\mu$l~10 $\mu$l blood) or a dried blood spot (DBS), the sensitivity of the test will be a limiting factor of a corresponding quantitative analytical method.

Aromatic compounds, also known as arenes or aromatics, are chemical compounds that contain conjugated planar ring systems. Typical aromatic compounds are benzene, phenol, aniline, and their derivatives. A great number of bioactive materials (including drugs) are aromatic compounds, such as estradiol, estriol, estrone, bilirubin, biliverdin, benzodiazepines, vitamin B1, vitamin B2, cannabinoids, etc. The LC-MS analysis of these compounds which form an important category of bioactive materials, is sometimes challenging because of required sensitivity levels. For example, as an estrogen hormone, estradiol is in low concentration in clinical samples, thus the LC-MS analytical method for estradiol requires ultra-high sensitivity. It was reported that using sulfonyl chloride to derivatize estradiol can enhance the LC-MS sensitivity, but this derivatization can only be applied to alcohol group-contained aromatic compounds (phenol derivatives). So far there has not been any report of derivatization approach for aromatic compounds with broad applicability.

SUMMARY

As set forth in the background section, a highly sensitive quantitative analytical method for analyzing aromatic compound is desirable, e.g., in clinical settings where the sample or analyte is of low quantity or low concentration (e.g., a small volume of blood, or estradiol in clinical samples) or when the sample is dry (e.g., a dry blood spot). Chemical derivatization (chemical modification of molecular structure) can sometimes be performed to produce a modified analyte which has high detectability, i.e. high ionization efficiency in LC-MS. The recent report of using sulfonyl chloride to derivatize estradiol to enhance the LC-MS sensitivity suffer from the shortcoming that this derivatization can only be applied to alcohol group-contained aromatic compounds (phenol derivatives) and that the reaction must be in the absence of water (e.g., water-containing sample must be dried) which increases the complexity of derivatization approach. Thus, it is highly desirable to have a generally applicable analytical method and system that is ease to use based on its compatibility with the presence of water in the sample. Allowing the analysis to proceed without having to first dry the water-containing sample can greatly shorten analysis time and the high requirement on the available quantity and concentration of the sample.

As disclosed herein, a method for analyzing aromatic compounds, including steps to: (a) prepare a diazonium reagent; (b) contact aromatic compounds in a sample with the diazonium reagent to form an analyte (e.g., derivatizing the aromatic compound using the diazonium reagent to form azo derivatives of one or more analytes); (c) measure an amount or ratio of the analyte (e.g., analyzing the azo derivatives of the one or more analytes in liquid chromatography-mass spectrometry (LC-MS) to obtain the relative concentration, abundance, and/or ratio of the analytes); and (d) extrapolating presence or quantity of the aromatic compounds in the sample based on the measured amount or ratio of the first analyte that has been formed.

In some embodiments, the diazonium reagent contains one or more aromatic functional groups.

In some embodiments, the diazonium reagent contains one or more phenyl groups.

In some embodiments, the contacting (e.g., derivatizing the aromatic compounds with the diazonium reagent) includes having azo coupling reaction between the diazonium reagent and the aromatic compounds, and the analyte is an azo-coupled analyte.

In some embodiments, the sample is in liquid form (e.g., the sample contains water, is an aqueous sample, and the sample is directly modified (e.g., derivatized) with diazonium reagent).

In some embodiments, the liquid sample contains a solvent, and the solvent consists of one or more of water and one or more organic solvents.

In some embodiments, the sample contains water, and the aqueous sample (e.g., sample is not dried first before the contacting with the diazonium reagent) is directly modified (e.g., derivatized with) the diazonium reagent.

In some embodiments, the diazonium reagent contains one or more functional groups that can be negatively charged during LC-MS analysis. In some embodiments, the diazonium reagent contains one or more functional groups that can be positively charged during LC-MS analysis. In some embodiments, In some embodiments, the diazonium reagent contains one or more functional groups that can be negatively or positively charged during LC-MS analysis. In some embodiments, the azo derivatives containing the functional groups is negatively charged, or positively charged through azo coupling reaction during LC-MS analysis. In some embodiments, the one or more functional groups in the diazonium reagent that are negatively charged are intrinsically negatively charged. In some embodiments, the one or more functional groups in the diazonium reagent that is negatively charged are ionized to be negatively charged during LC-MS analysis. In some embodiments, the one or more functional groups in the diazonium reagent that are positively charged are intrinsically positively charged. In some embodiments, the one or more functional groups in the diazonium reagent that are positively charged are protonated to be positively charged during LC-MS analysis.

In some embodiments, the one or more functional groups (e.g., the intrinsically negatively charged functional groups)

include one or more of, but are not limited to sulfonate group ($-SO_3^-$) and carboxylate group ($-COO^-$). In some embodiments, the one or more functional groups (the ionized to be negatively charged functional groups) include one or more of, but are not limited to, sulfonic acid group ($-SO_3H$) and carboxylic acid group ($-COOH$). In some embodiments, the one or more functional groups include one or more of sulfonate group ($-SO_3^-$), carboxylate group ($-COO^-$), sulfonic acid group ($-SO_3H$), and carboxylic acid group ($-COOH$).

In some embodiments, the one or more functional groups (e.g., the intrinsically positively charged functional groups) include one or more of, but are not limited to quaternary ammonium group. In some embodiments, the one or more functional groups (e.g., the protonated to be positively charged functional groups) include one or more of, but are not limited to, amino group and thiol group. In some embodiments, the one or more functional groups include one or more of quaternary ammonium group, amino group and thiol group.

In some embodiments, a quencher is added to the sample after contacting the aromatic compounds with the diazonium reagent (e.g., to quench the unreacted diazonium reagent). Such quencher reacts with the diazonium group ($-N_2^+$) to form a quenching product, thus eliminating the unreacted diazonium reagent.

In some embodiments, the quencher includes one or more of, but is not limited to, ascorbic acid, organic halides, aliphatic compounds with active methylene groups.

In some embodiments, the quencher is an aromatic compound distinct from the aromatic compound(s) present in the sample.

In some embodiments, the quencher includes one or more of, but is not limited to, phenol, phenol derivatives, naphthol, naphthol derivatives, and aniline derivatives.

In some embodiments, the quencher is an aromatic compound containing one or more electron-donating groups.

In an aspect, a reagent kit for LC-MS analysis of aromatic compounds is disclosed, including a diazonium reagent (e.g., used to react with aromatic compounds in a sample), wherein the diazonium reagent is a diazonium salt that contains a diazonium ion, and/or one or more materials to prepare the diazonium reagent (e.g., an amine and nitrous acid, and/or a nitrite and an acid).

In some embodiments, the diazonium reagent contains one or more aromatic functional groups.

In some embodiments, the diazonium reagent contains one or more phenyl groups.

In some embodiments, the diazonium reagent contains one or more functional groups that are negatively charged during LC-MS analysis. In some embodiments, the diazonium reagent contains one or more functional groups that are positively charged during LC-MS analysis. In some embodiments, the one or more functional groups in the diazonium reagent that are negatively charged are intrinsically negatively charged. In some embodiments, the one or more functional groups in the diazonium reagent that are negatively changed are ionized to be negatively charged during LC-MS analysis. In some embodiments, the one or more functional groups in the diazonium reagent that are positively charged are intrinsically positively charged. In some embodiments, the one or more functional groups that are positively charged are protonated to be positively charged during LC-MS analysis.

In some embodiments, the one or more functional groups (e.g., the intrinsically negatively charged functional groups) include one or more of, but are not limited to sulfonate group ($-SO_3^-$) and carboxylate group ($-COO^-$). In some embodiments, the one or more functional groups (e.g., the ionized to be negatively charged functional groups) include one or more of, but are not limited to, sulfonic acid group ($-SO_3H$) and carboxylic acid group ($-COOH$).

In some embodiments, the one or more functional groups (e.g., the intrinsically positively charged functional groups) include one or more of, but are not limited to quaternary ammonium group. In some embodiments, the one or more functional groups (e.g., the protonated to be positively charged functional groups) include one or more of, but are not limited to, amino group and thiol group.

In some embodiments, the materials to prepare the diazonium reagent include an amine and nitrous acid or the materials to prepare them; the materials to prepare nitrous acid include a nitrite and an acid.

In some embodiments, the reagent kit further includes (e.g., further consists of) one or more items of a sample extraction solvent, a sample reconstitution solvent, a sample precipitant, a sample diluent, a sample elution solvent, one or more internal standards, one or more calibrators, and a quencher to quench unreacted portion of the diazonium reagent.

The derivatization-based analytical method for aromatic compounds described in this disclosure is based on azo coupling reaction of analytes. The azo coupling reaction links an additional moiety to an analyte molecule through the formation of an azo group ($-N=N-$). The produced azo derivative of the analytes contains the additional moiety, which is a chemical structure easily to be charged. The modification of the analytes in this manner increases its ionization propensity thus enhances its ionization efficiency in LC-MS analysis.

In some embodiments, the azo group in the azo derivatives is resulted from the azo coupling reaction, as a linkage between the original analyte molecule and the additional moiety. The additional moiety may contain one or more functional groups that are negatively or positively charged during LC-MS analysis, thus enhancing the ionization efficiency in LC-MS analysis in negative-ion mode or positive-ion mode.

If the diazonium reagent contains one or more functional groups that can be negatively charged, the azo derivatives formed through derivatization of the aromatic compounds in the sample consequently contain such functional groups and can be negatively charged during LC-MS analysis, enhancing their ionization efficiency in negative-ion mode. Usually negative-ion mode LC-MS analysis is less affected by interferents resulting in lower impact of background noise, thus making analytes negatively charged is advantageous in analyzing complex-matrix samples such as blood or serum samples because the detection sensitivity is enhanced. If the diazonium reagent contains one or more functional groups that can be positively charged, the azo derivative formed through derivatization of the analytes consequently contain such functional groups and can be positively charged during LC-MS analysis, further enhancing their ionization efficiency in positive-ion mode LC-MS.

The azo group in the azo derivatives is composed of two nitrogen atoms which may be protonated to be positively charged. In positive-ion mode LC-MS analysis, this feature of the azo group enhances ionization efficiency of the azo derivatives. Thus, even if the additional moiety from the diazonium reagent does not contain a functional group that may be positively charged, the ionization efficiency of the azo derivative is still enhanced in positive-ion mode LC-MS analysis due to the presence of the azo group.

Aromatic compounds contain conjugated planar ring systems, i.e. aromatic functional groups. Aromatic functional groups have common chemical properties such as a propensity to electrophilic aromatic substitution reactions. Azo coupling reaction is a type of electrophilic aromatic substitution reactions. Thus, this derivatization approach is generally applicable to all kinds of aromatic compounds that have the azo coupling reaction, resulting in broad applicability of this high sensitivity analytical method, not just for detecting aromatic compound using LC-MS analysis.

The azo coupling reaction takes place in aqueous phase or organic phase or miscible mixed organic-aqueous phase. It can be directly (e.g., without first performing a drying/dehydrating procedure on the sample) applied to water-containing samples, such as clinical samples in whole blood, plasma, serum, saliva, urine, etc. Most derivatization approaches in LC-MS analytical methods employ organic-phase reactions, requiring sample drying during sample preparation. In contrast, this high sensitivity analytical method is simple and easy-to-use with samples in the aqueous, organic, and/or mixed organic aqueous phase, saving sample processing time and manual steps thus reducing the possibility of user error and sample loss.

Reported in this disclosure, the reagent kit for analysis of aromatic compounds provides some or all of the advantages of the derivatization-based analytical method reported in this disclosure, resulting in rapidity and convenience in user operation, in particular for LC-MS analysis.

DETAILED DESCRIPTION

In order to explain the purposes, protocols, and results of the disclosed method and system, the following contents are described with the use of the figures. It should be noted that the examples described here are only used for the explanation of the disclosed technique and system, not to limit the scope of this disclosure.

Figure 1:
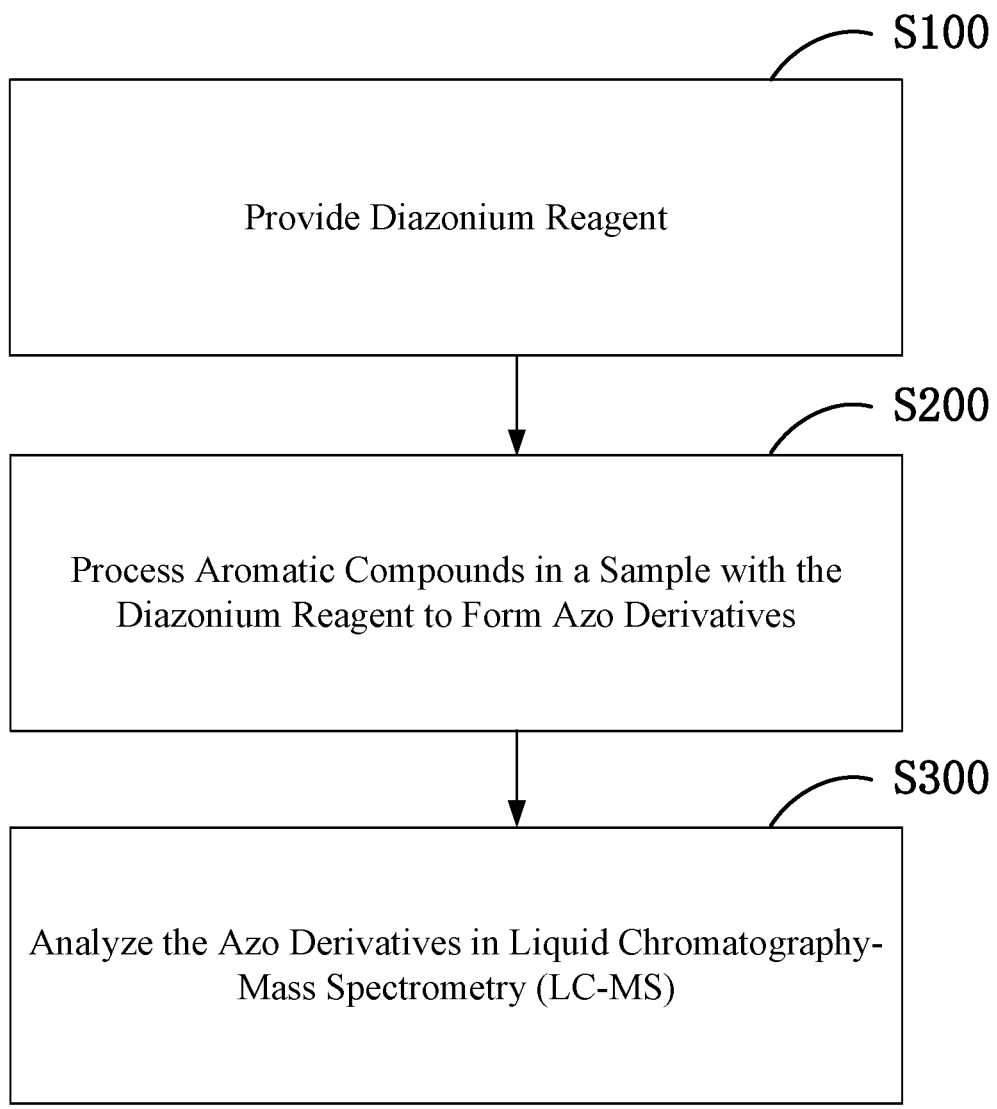
FIG. 1 illustrates the procedure of derivatization and LC-MS analysis of aromatic compounds in accordance with some embodiments.

As illustrated in FIG. 1, the derivatization-based analytical method includes:

S100, prepare a diazonium reagent;

S200, process aromatic compounds (e.g., derivatize aromatic compounds) in a sample with the diazonium reagent to form azo derivatives of analytes; and S300, analyze the azo derivatives of analytes in liquid chromatography-mass spectrometry (LC-MS).

The aromatic compounds in samples are targets of analysis, or analytes. The derivatization-based analytical method for aromatic compounds described in this disclosure is based on azo coupling reaction of analytes. The azo coupling reaction links an additional moiety to an analyte molecule through the formation of an azo group (—N=N—). The produced azo derivative of the analyte (e.g., the azo derivative of the original target analyte is a modified analyte that is measured in LC-MS) contains the additional moiety, which can be a chemical structure easily to be charged. The modification of the analyte increases its ionization propensity thus enhances its ionization efficiency in LC-MS analysis.

The azo group in the azo derivative is composed of two nitrogen atoms which can be protonated to be positively charged. In positive-ion mode LC-MS analysis, this feature enhances ionization efficiency. Thus, even if the additional moiety from the diazonium reagent does not contain a functional group that can be positively charged, the ionization efficiency of the azo derivative is still enhanced in positive-ion mode LC-MS analysis due to the presence of the azo group.

Aromatic compounds contain conjugated planar ring systems, i.e. aromatic functional groups. An aromatic functional group of an target analyte may be any derivative from a simple aromatic ring, in accordance with some embodiments. Simple aromatic rings include, but are not limited to, six-member aromatic rings such as benzene ring, pyridine ring, pyrazine ring, pyrimidine ring, pyridazine ring, triazine ring, five-member aromatic rings such as furan ring, pyrrole ring, pyrazole ring, imidazole ring, triazole ring, tetrazole ring, oxazole ring, oxadiazole ring, thiophene ring, thiazole ring, thiadiazole ring, etc., in accordance with various embodiments. Aromatic functional groups have common chemical properties such as propensity to electrophilic aromatic substitution reactions. Azo coupling reaction is a type of electrophilic aromatic substitution reactions. Thus, this derivatization approach is generally applicable to all kinds of aromatic compounds that have azo coupling reactions, resulting in broad applicability of this high sensitivity analytical method.

The azo coupling reaction takes place in aqueous phase or organic phase or miscible mixed organic-aqueous phase. The disclosed method can be directly applied to water-contained samples, such as clinical samples in whole blood, plasma, serum, saliva, urine, etc., in accordance with some embodiments. Most derivatization approaches in LC-MS analytical methods employ organic-phase reactions, requiring sample drying during sample preparation. In contrast, this high sensitivity analytical method is simple and easy-to-use, saving sample processing time and manual steps thus reducing the possibility of user error and sample loss.

In some embodiments of step S100, the diazonium reagent contains one or more aromatic functional groups. In some embodiments, the diazonium reagent contains one or more phenyl groups, but not limited to phenyl groups.

In some embodiments, the diazonium reagent contains one or more functional groups that can be negatively charged during LC-MS analysis. Through azo coupling reaction, the azo derivatives contain such functional groups that can be negatively charged during LC-MS analysis.

The functional groups in the diazonium reagent that may be negatively charged are either intrinsically negatively charged or ionized to be negatively charged during LC-MS analysis. The intrinsically negatively charged functional groups include one or more of, but are not limited to sulfonate group (—SO3—) and carboxylate group (—COO—), and the ionized to be negatively charged functional groups include one or more of, but are not limited to sulfonic acid group (—SO3H) and carboxylic acid group (—COOH). Sulfonic acid group (—SO3H) and carboxylic acid group (—COOH) can ionize in organic phase or aqueous phase to be negatively charged. Usually negative-ion mode LC-MS analysis is less affected by interferents resulting in lower background noise, thus making analytes negatively charged is advantageous in analyzing complex-matrix samples such as blood or serum samples.

In some embodiments, the diazonium reagent contains one or more functional groups that may be positively charged during LC-MS analysis. Through azo coupling reaction, the azo derivatives contain the functional groups that may be positively charged during LC-MS analysis.

The functional groups in the diazonium reagent that may be positively charged are either intrinsically positively charged, or protonated to be positively charged during LC-MS analysis. The intrinsically positively charged functional groups include one or more of, but are not limited to quaternary ammonium group, and the protonated to be positively charged functional groups include one or more of, but are not limited to amino group and thiol group. In quaternary ammonium group (—NR3+), the R groups linked to the N atom may be the same or different in various embodiments. Amino group is primary amino group (—NH2), secondary amino group (—NHR), or tertiary amino group (—NR2+), in which the R groups linked to the N atom are the same or are different in various embodiments. Thiol group is sulfhydryl group (—SH) or thioether group (—SR), in various embodiments.

In some embodiments, the diazonium reagent contains one or more other functional groups, such as alkyl group, alkenyl group, alkynyl group, alkoxy group, alcohol group, carbonyl group, phosphate group, halogen group, etc. The functional groups link to an aromatic functional group through any number and type of chemical bonds, typically through a σ single bond, in various embodiments.

In some embodiments of step S100, the diazonium reagent is directly provided (e.g., in the kit). In some embodiments, the materials to prepare the diazonium reagent are provided (e.g., in the kit), and the diazonium reagent is prepared on site (e.g., immediately prior to analysis).

In some embodiments, the diazonium reagent is prepared by diazotization reaction of an amine and nitrous acid. The materials to prepare diazonium reagent include but are not limited to an amine, a solvent, nitrous acid or materials to prepare nitrous acid.

In some embodiments, the amine to prepare diazonium reagent is an arylamine, such as aniline, o-/p-sulfanilic acid, o-/p-nitroaniline, and/or dichloroaniline, etc.

Nitrous acid is typically unstable. In some embodiments of step S100, nitrous acid is prepared from precursor materials one site, and then reacts with amine to prepare diazonium reagent immediately prior to the analysis. The precursor materials include a nitrite and an acid. The acid is one or more of hydrochloric acid, hydrobromic acid, sulfuric acid, nitric acid, and/or phosphoric acid, etc. The nitrite can be one or more of sodium nitrite, potassium nitrite, etc., in accordance with various embodiments.

In some embodiments, the solvent to prepare diazonium reagent includes but are not limited to water, sodium hydroxide solution, or sodium bicarbonate solution. The basic solutions dissolves amino group-contained acid such as sulfanilic acid, to prevent precipitation of inner salt formed in acidic environment, in some embodiments.

In some embodiments, the amine and nitrite used to prepare the diazonium reagent are pre-mixed in solid form (e.g., in the kit), and when it is in use, an acid is added to prepare diazonium reagent in one step.

In some embodiments of step S200, derivatizing aromatic compounds with the diazonium reagent includes enabling azo coupling reaction between the diazonium reagent and the aromatic compounds in the sample. In some embodiments, the azo coupling reaction between the diazonium reagent and the aromatic compounds is described in the chemical equation below.

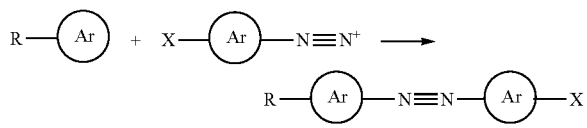

In some embodiments, the azo coupling reaction between the diazonium reagent and aromatic compounds is described in the chemical equation below.

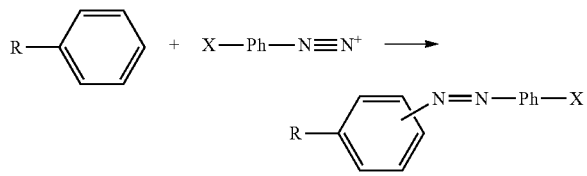

In some embodiments of step S200, the sample contains water. The azo coupling reaction is directly applied to water-contained samples, such as clinical samples in whole blood, plasma, serum, saliva, urine, etc. Most derivatization approaches in LC-MS analytical methods employ organic-phase reactions, requiring sample drying during sample preparation. In contrast, this high sensitivity analytical method is simple and easy-to-use, saving sample processing time and manual steps thus reducing possibility of user error and sample loss. The matrix of a water-containing sample may be completely aqueous or miscible mixed organic-aqueous phase, in some embodiments. A water-containing sample may be a processed sample or an unprocessed neat sample, in some embodiments. Here sample processing includes but are not limited to precipitation, centrifuge, filtration, concentration, etc., in some embodiments In some embodiments, an additional step S400 is applied after step S200: adding a quencher to the sample after processing the aromatic compounds with the diazonium reagent to quench the unreacted diazonium reagent. The quencher may react with diazonium group (—N2+) to form a quenching product, thus eliminating the unreacted diazonium reagent, in some embodiments. The quenching step may prevent possible interference of the diazonium reagent to the following analysis, if there is any, in some embodiments.

In some embodiments, the quencher is an aromatic compound. In some embodiments, the quencher is an aromatic compound with one or more electron-donating groups on aromatic rings. Electron-donating groups may increase the density of electron cloud at certain positions of aromatic rings, enhancing the electrophilic substitution reaction activity. The ortho- and para-positions of an electron-donating group are increased more significantly, thus tend to have electrophilic substitution. Using aromatic compounds with electron-donating groups to quench the unreacted diazonium reagent facilitates efficient quenching reaction and makes the quenching reaction complete. In some embodiments, to make the quenching reaction complete excess amount of quencher is added to the container, if the quencher is not highly active. The aromatic compound used as the quencher is distinct from the target analytes, and includes but is not limited to phenol, phenol derivatives such as salicylic acid, naphthol, naphthol derivatives, aniline derivatives such as N,N-dimethylaniline, etc.

The quencher is not limited to aromatic compounds, as long as it consumes the diazonium group (—N2+) in the diazonium reagent, in some embodiments. In some embodiments, the quencher and the diazonium reagent react to produce a stable product which is distinguished from the azo derivatives of analytes in LC-MS analysis. The quencher includes but is not limited to ascorbic acid, organic halides, aliphatic compounds with active methylene groups, etc., in some embodiments.

To further eliminate the effect of the quenching product to LC-MS analysis, the quenching product is diverted to side flowpath in the LC-MS analysis step of S300, based on its different chromatographic elution time compared to that of the analytes, in some embodiments. Thus, the quenching product does not enter mass spectrometer to affect LC-MS analysis, and the mass spectrometer only performs measurements on the derivatized target analytes.

It should be noted that step S400 is not a necessary step, in some embodiments. If step S400 is not carried out, it is possible to use other means to eliminate the effect of the unreacted diazonium reagent to LC-MS analysis, in some embodiments. In some embodiments, the unreacted diazonium reagent is diverted to a side flowpath, based on its different chromatographic elution time compared to that of the analytes (e.g., the original and the modified analytes). Thus, the unreacted diazonium reagent does not enter mass spectrometer to affect LC-MS analysis.

In step S300, in some embodiments, single ion monitoring (SIM) or multiple reaction monitoring (MRM) (also named as selected reaction monitoring) scan type is employed in LC-MS analysis—typically using MRM scan type results in higher sensitivity than using SIM scan type in an analytical method.

Step S300, in some embodiments, includes actions to quantitatively analyze the concentrations of analytes, for example using internal standard-free quantitative analysis or internal standard-added quantitative analysis.

An internal standard is a compound with similar chemical properties to an analyte (typically a structural analog or a stable isotope-labeled analyte), which is added to samples in a constant amount to correct for analyte loss during sample preparation and variation of ionization efficiency in LC-MS analysis.

In some embodiments, the quantitative analysis actions include:

S310, provide a quantitative relationship between (1) LC-MS signals of azo derivatives of analytes in calibrators and (2) corresponding analyte concentrations of the analytes used in the calibrators;

S320, implement LC-MS analysis of the test samples containing azo derivatives of target analytes, and measure the LC-MS signals of the azo derivatives of the target analytes in the test sample; and S330, obtain the target analyte concentrations in the test samples by using the LC-MS signals of the azo derivatives of the target analytes in the test sample and the provided quantitative relationship.

In internal standard-free quantitative analysis, LC-MS signal refers to the peak area of a target of detection in ion chromatogram, in some embodiments. In internal standard-added quantitative analysis, LC-MS signal refers to the peak area ratio of a target of detection to its corresponding internal standard in ion chromatogram, in some embodiments. A target of detection is an ionized molecule detected in LC-MS analysis, and in this disclosure it is either an analyte or an azo derivative of the analyte.

In some embodiments, calibrators are standard samples with known analyte concentrations, say multiple solutions with known analyte concentrations are prepared to be used as calibrators. The analytes are native compounds, before derivatization.

In some embodiments, the quantitative relationship between LC-MS signals of azo derivatives of analytes in calibrators and measured analyte concentrations is obtained through the following actions:

S311, prepare multiple calibrators with different analyte concentrations of an analyte, and derivatize the analyte in the multiple calibrators, respectively, using the diazonium reagent;

S312, implement LC-MS analysis of the derivatized calibrators, and measure the LC-MS signals of the azo derivatives of analytes in the multiple calibrators;

S313, carry out curve fitting using the measured LC-MS signals for the multiple calibrators and known analyte concentrations in the multiple calibrators, and obtain a mathematical function of the LC-MS signal-analyte concentration relationship.

The calibrators and test samples are processed using the same protocol and diazonium reagent and analyzed under identical LC-MS conditions, in some embodiments.

The mathematical function is a linear, quadratic, or logarithmic function, in various embodiments. A successful curve fitting proves that a functional relationship exists between LC-MS signals and analyte concentrations for an analyte. Then it is possible to obtain analyte concentrations for that analyte in test samples through quantitative analysis. For example, if a linear function is obtained through curve fitting, it shows that linear relationship exists between LC-MS signals and analyte concentrations of the analyte in test samples.

In some embodiments, in step S330, analyte concentrations in test samples are obtained by interpolating the LC-MS signals into the functional relationship for the target analyte in the test sample.

It should be noted that in a derivatization-based analytical method, while LC-MS signal is measured on the derivatives of an analyte, analyte concentration of the analyte refers to the concentration of the analyte before the derivatization of the analyte, i.e. the native analyte concentration. It is because (1) native analyte is the target of the analysis, and (2) the derivative concentration is proportionally related to the native analyte concentration, so the LC-MS signal-analyte concentration relation is mathematically consistent when using either the derivative concentration or the native analyte concentration. In the embodiments above, the calibrators are provided in the form of native analytes, which are derivatized using the same protocol and diazonium reagent and analyzed under identical LC-MS conditions as the test samples. On the other hand, if the calibrators are derivatized using a different protocol from the test samples, for instance a dilution solvent is added into one of the two, then in step S330 the values obtained by function interpolation is converted to analyte concentrations using the dilution factor. In addition, when internal standard-added quantitative analysis is used, the internal standard is preferably a compound that is not derivatized. Thus, the internal standard is added into samples before step S200, and derivatized together with the analytes in step S200, in some embodiments.

In one aspect, a reagent kit for LC-MS analysis of aromatic compounds, including a diazonium reagent to react with aromatic compounds in a sample, is disclosed. The diazonium reagent is either a diazonium salt that contains a diazonium ion to derivatize analytes, or one or more materials to prepare the diazonium reagent during the analysis procedure, in some embodiments.

In some embodiments, the reagent kit for LC-MS analysis of aromatic compounds provides all the advantages of the derivatization-based analytical method described herein, and is configured and provided to enable the method described herein to be carried out, resulting in rapidity and convenience in user operation. The various details described above with respect to the method of analysis applies to the reagent kit and usage of the reagent kit as well, and are not repeated in the interest of brevity.

In some embodiments, the reagent kit includes (e.g., consists of), in addition to the diazonium reagent, one or more items of a sample extraction solvent, a sample reconstitution solvent, a sample precipitant, a sample diluent, a sample elution solvent, a internal standards, one or more calibrators, and a quencher to quench unreacted diazonium reagent. Sample extraction solvent is provided and used to extract analytes from complex-matrix samples, such as dried blood spot (DBS) samples, in some embodiments. Sample reconstitution solvent is provided and used to reconstitute dry samples, such as nitrogen-dried samples or dried blood spot (DBS) samples, in some embodiments. Sample precipitant is provided and used to precipitate to remove unwanted components in the matrix of samples, such as proteins in serum samples, in some embodiments. Sample diluent is provided and used to properly dilute samples for further sample processing, in some embodiments. Sample elution solvent (also named as mobile phase) is provided and used in LC-MS analysis to elute analytes from liquid chromatograph and carry them into mass spectrometer, in some embodiments. Mobile phase includes, but is not limited to, water, buffer salts, acid, base, methanol, acetonitrile, etc., in some embodiments. Internal standards and calibrators are provided and used in quantitative analysis of samples, in some embodiments. Quencher is provided and used as described in step S400, in some embodiments.

EXAMPLES

The examples below describe further details of various embodiments. While embodiments of the present disclosure are described in connection with the examples and the corresponding text and figures, there is no intent to limit embodiments of the disclosure to these descriptions. On the contrary, the intent is to cover all alternatives, modifications, and equivalents included within the spirit and scope of embodiments of the present disclosure. The different options described in the various examples may be used independently or in combination in various embodiments. The quantities quoted in the various examples are illustrative of the reactions that take place in the processes and a person skilled in the art will understand extrapolations and scaling of these quantities to other usage scenarios, without undue efforts. The following examples describe analysis of derivatized analytes relative to underivatized analytes, illustrating the enhanced sensitivity of the test based on derivatization of analytes. In practice, analysis on underivatized analytes need not be performed when analyzing real samples.

Example 1

Preparation of Diazonium Reagent

Option 1

(1) Measure 31.5 mg p-sulfanilic acid powder and dissolve it in 15 ml 1% sodium hydroxide solution.

(2) Add 12 mg sodium nitrite powder and 3.0 ml 1.0 M HCl solution to prepare p-sulfanilic acid diazonium salt solution.

Option 2

(1) Measure 21 mg p-sulfanilic acid powder and dissolve it in 10 ml 1% sodium hydroxide solution.

(2) Add 8.0 mg sodium nitrite powder and 2.0 ml 1.0 M HCl solution to prepare p-sulfanilic acid diazonium salt solution.

Option 3

(1) Mix 21 mg p-sulfanilic acid powder and 8.0 mg sodium nitrite powder.

(2) Add 5.0 ml 0.10 mM HCl solution to prepare p-sulfanilic acid diazonium salt solution.

Example 2

Derivatization of Estradiol Using p-Sulfanilic Acid Diazonium Salt

S100, prepare p-sulfanilic acid diazonium salt solution.

S200, derivatize the aromatic compound estradiol in a sample using the prepared diazonium salt solution. The sample is made by dissolving estradiol in pure methanol at a concentration of 5.0 µg/ml. The reaction equation is shown below.

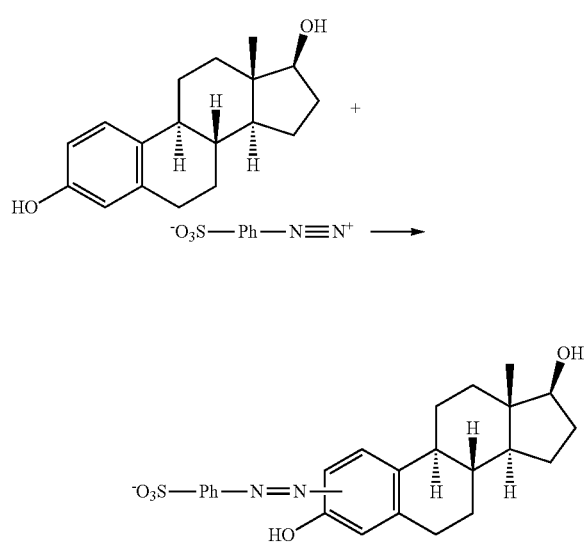

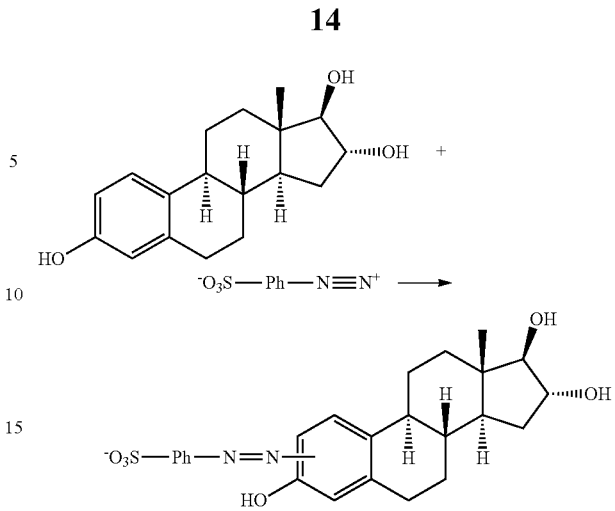

S300, analyze both the derivatized estradiol sample and the native estradiol sample in LC-MS.

Figure 2:
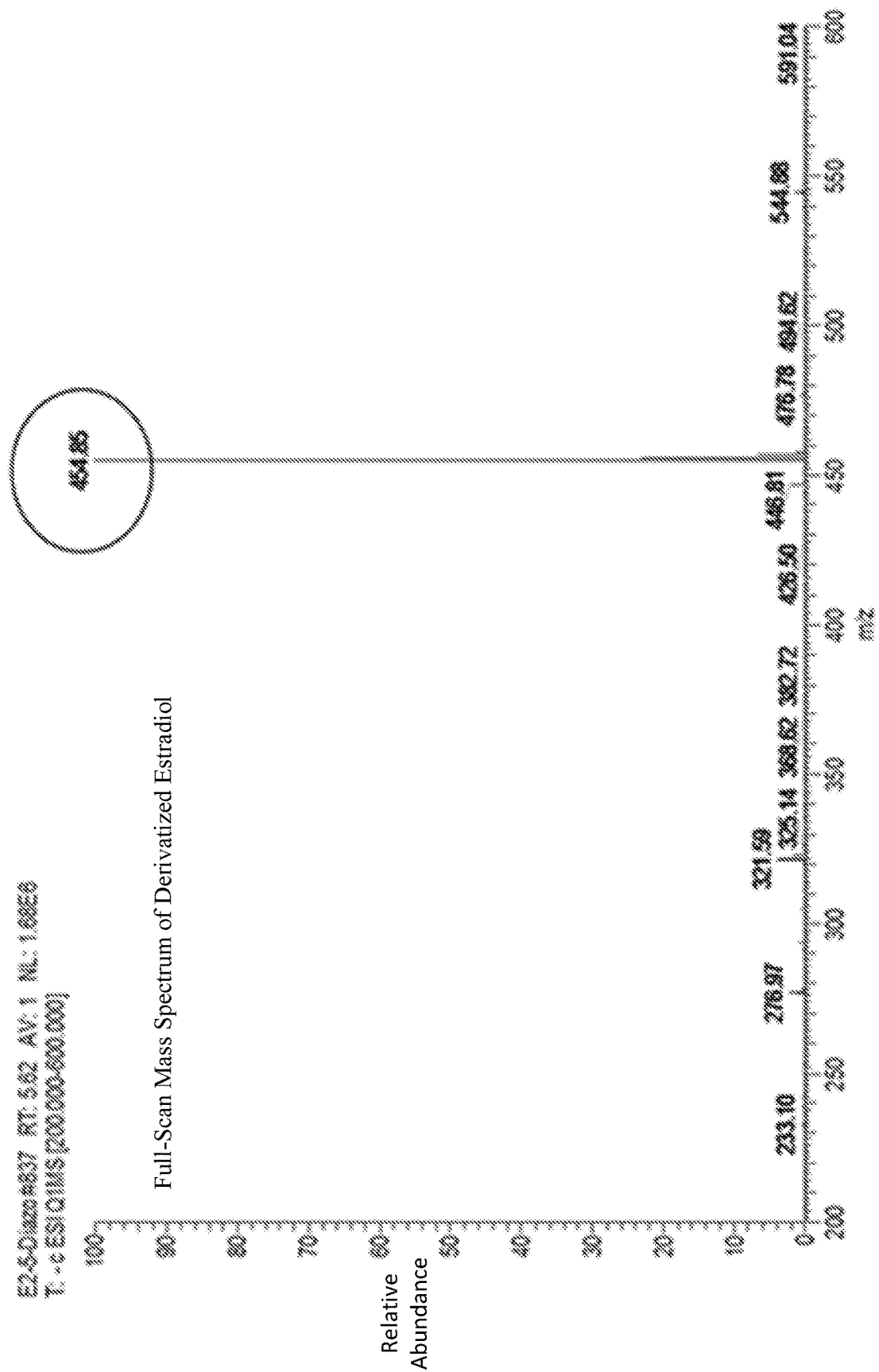
FIG. 2 shows a full-scan mass spectrum of p-sulfanilic acid diazonium-derivatized estradiol in Example 2, in accordance with some embodiments.
Figure 3:
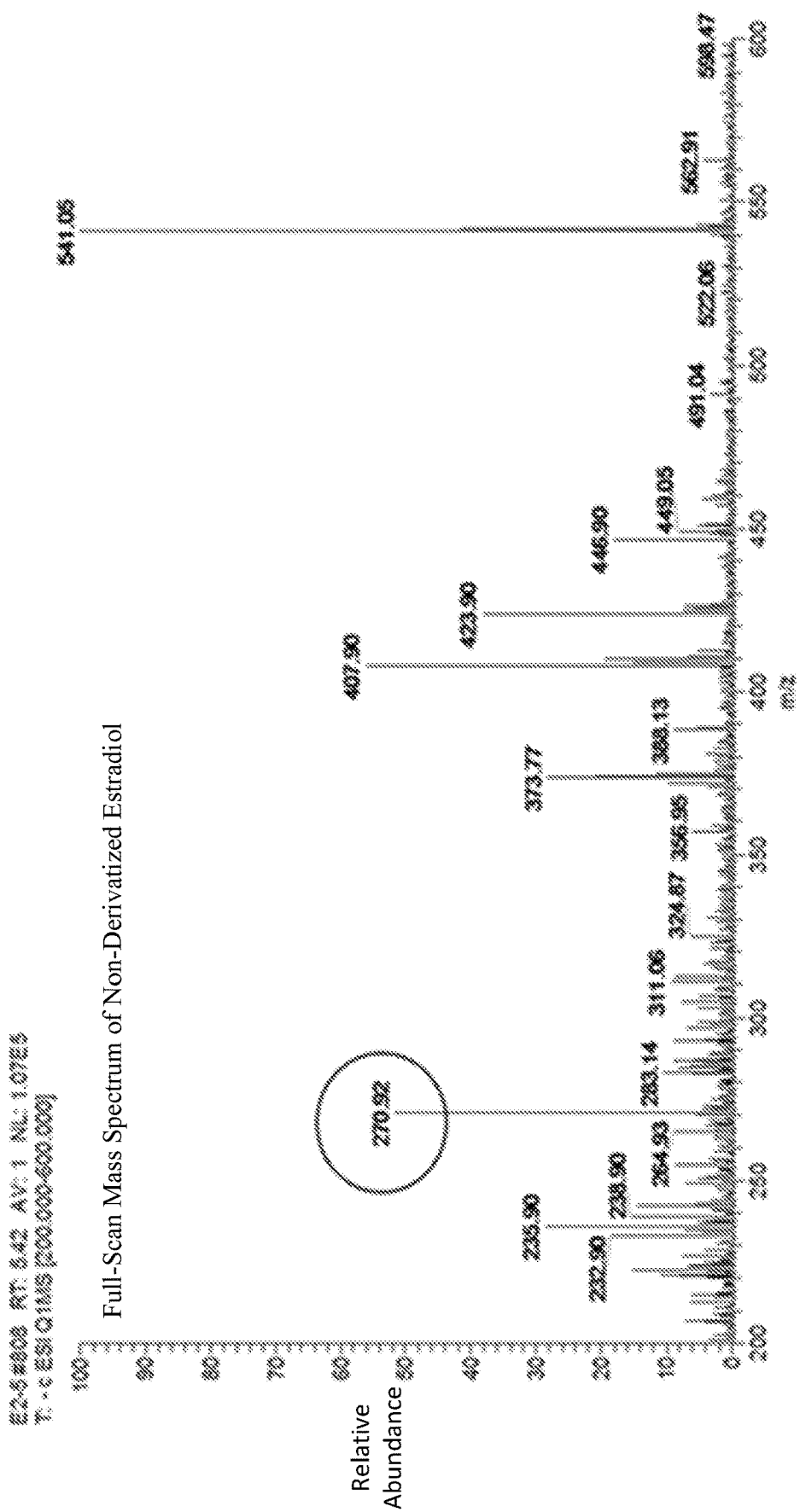
FIG. 3 shows a full-scan mass spectrum of native estradiol in Example 2, in accordance with some embodiments.
Figure 4:
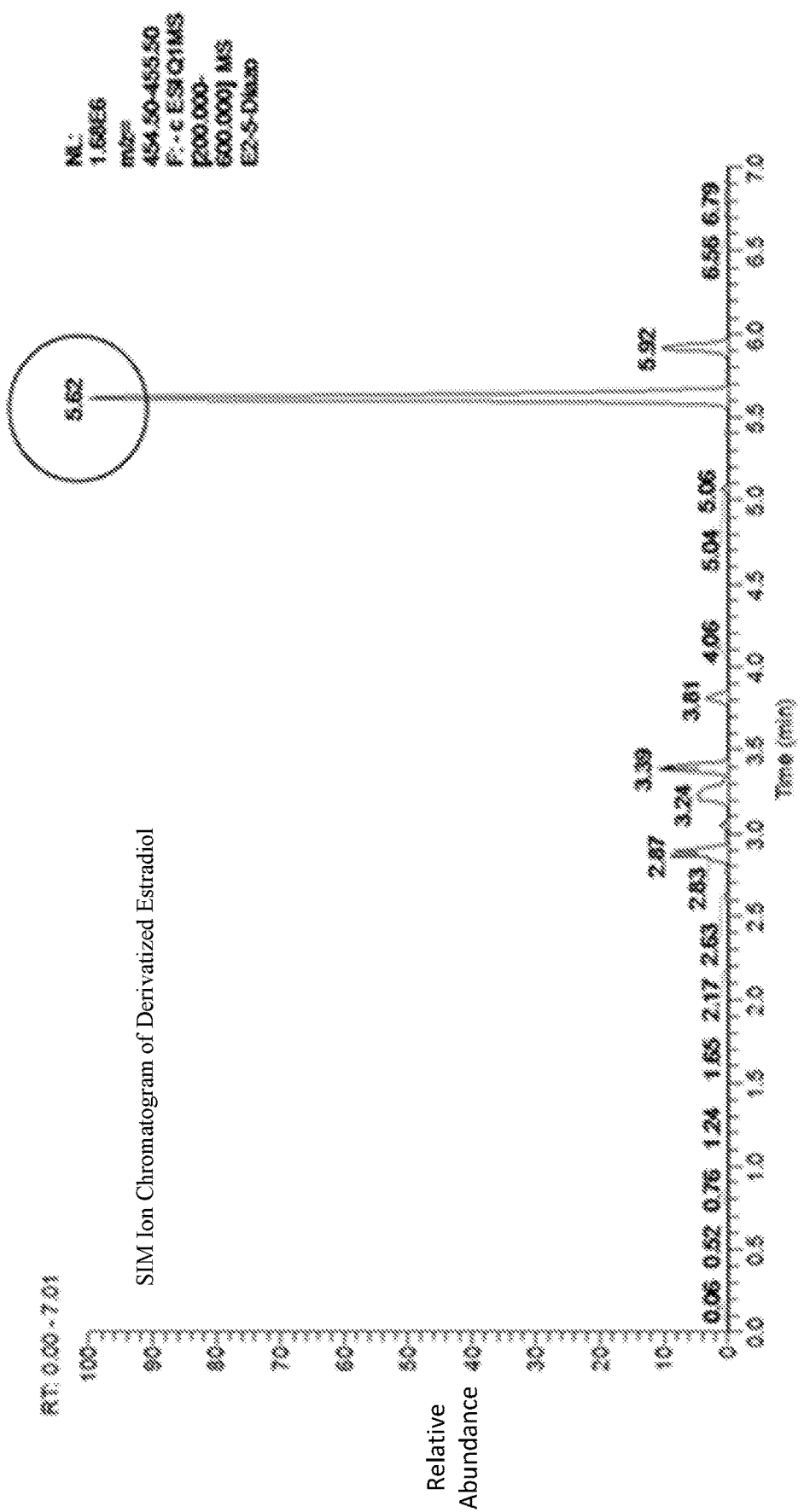
FIG. 4 shows a single ion monitoring (SIM) ion chromatogram of p-sulfanilic acid diazonium-derivatized estradiol in Example 2, in accordance with some embodiments.
Figure 5:
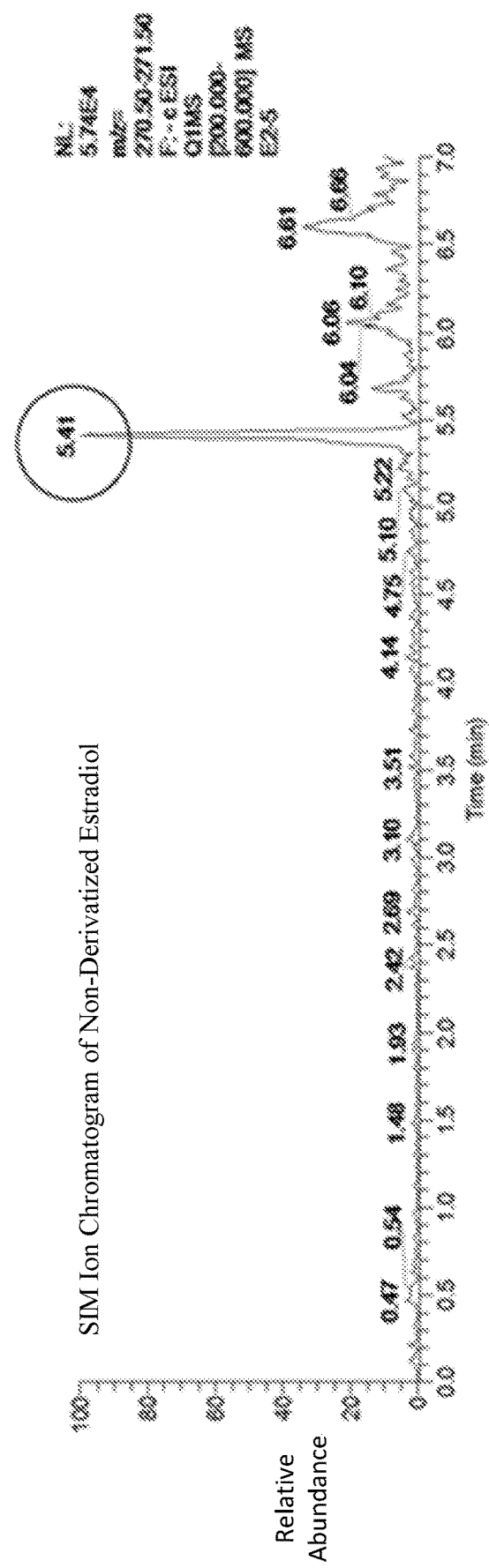
FIG. 5 shows a SIM ion chromatogram of native estradiol in Example 2, in accordance with some embodiments.

Referring to FIG. 2 FIG. 4, in negative-ion mode, full-scan mass spectrum is first used to identify the azo derivative of estradiol in the derivatized estradiol sample (e.g., circled peak signal in FIG. 2), and then single ion monitoring (SIM) is used to measure its LC-MS signal (e.g., circled peak signal in FIG. 4) in a quantitative manner. Referring to FIG. 3 and FIG. 5, in negative-ion mode, full-scan mass spectrum is first used to identify estradiol in the native estradiol sample (e.g., circled peak signal in FIG. 3), and then single ion monitoring (SIM) is used to quantitatively measure its LC-MS signal (internal standard-free quantitative analysis) (e.g., circled peak signal in FIG. 5). By comparison, the LC-MS signal of the azo derivative of estradiol (FIG. 4) is significantly higher than that of estradiol (FIG. 5).

Example 3

Derivatization of Estriol Using p-Sulfanilic Acid Diazonium Salt

S100, prepare p-sulfanilic acid diazonium salt solution.

S200, derivatize the aromatic compound estriol in a sample using the prepared diazonium salt solution. The sample is made by dissolving estriol in pure methanol at a concentration of 5.0 µg/ml. The reaction equation is shown below.

S300, analyze both the derivatized estriol sample and the native estriol sample in LC-MS.

Figure 6:
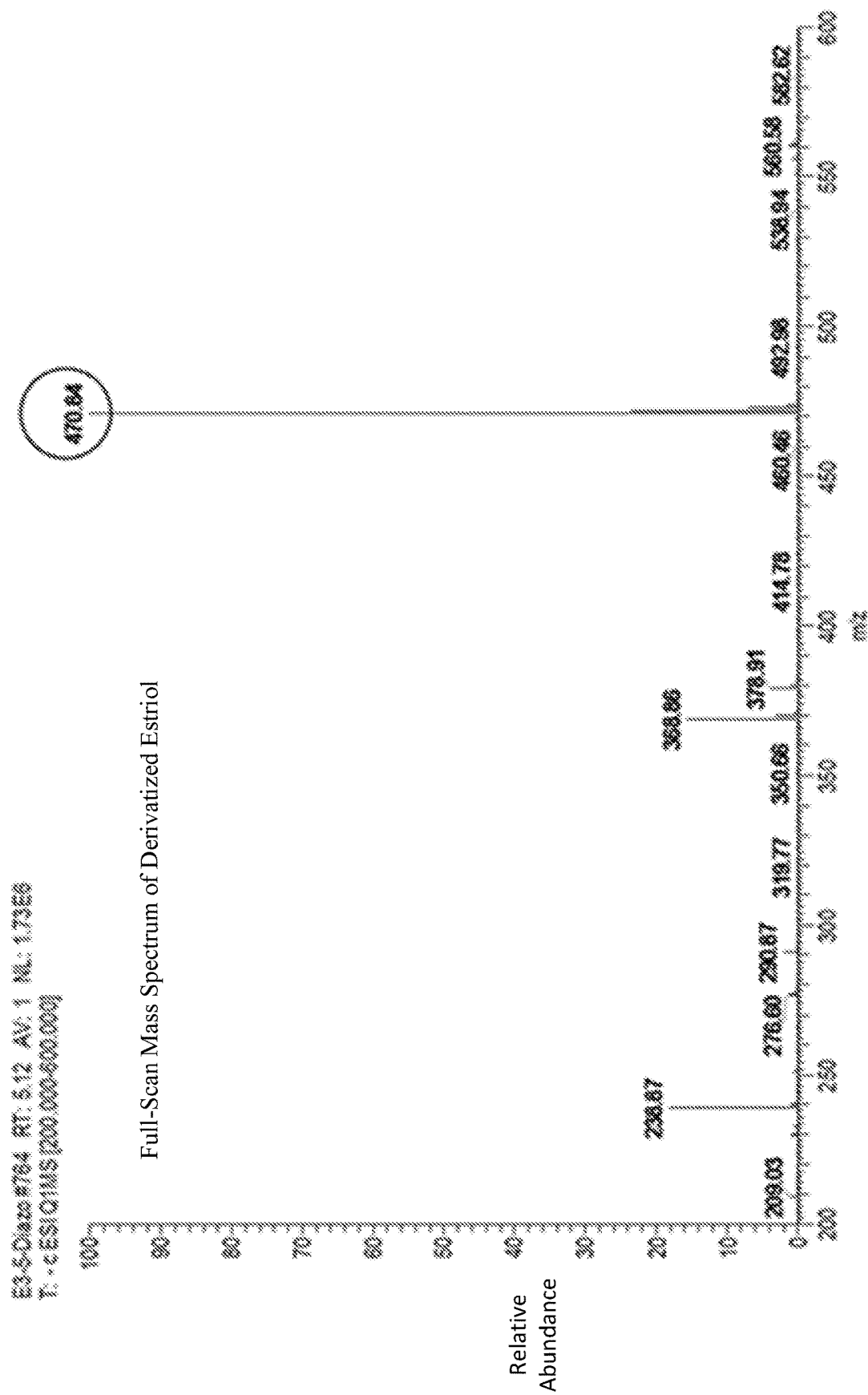
FIG. 6 shows a full-scan mass spectrum of p-sulfanilic acid diazonium-derivatized estriol in Example 3, in accordance with some embodiments.
Figure 7:
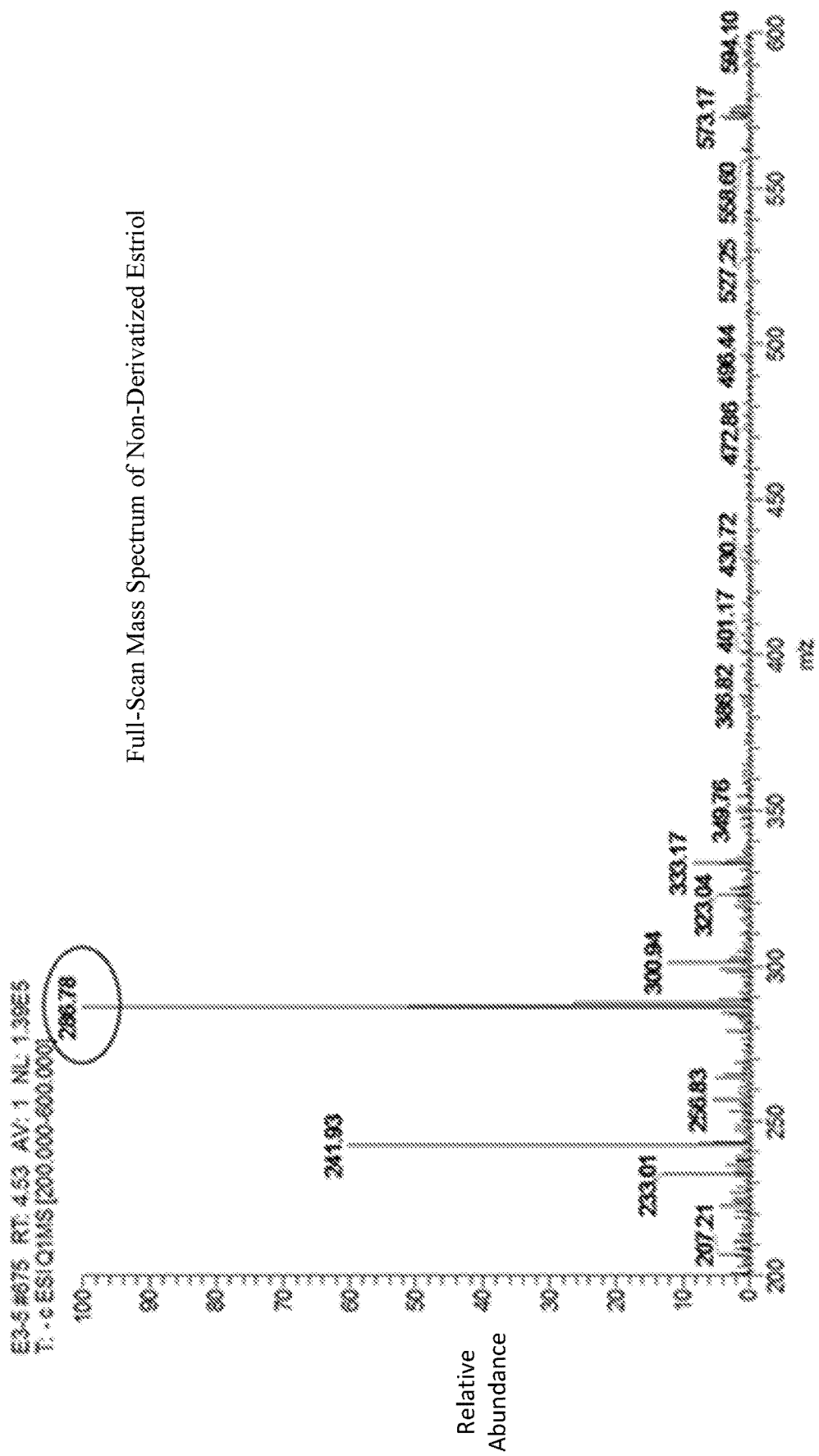
FIG. 7 shows a full-scan mass spectrum of native estriol in Example 3, in accordance with some embodiments.
Figure 8:
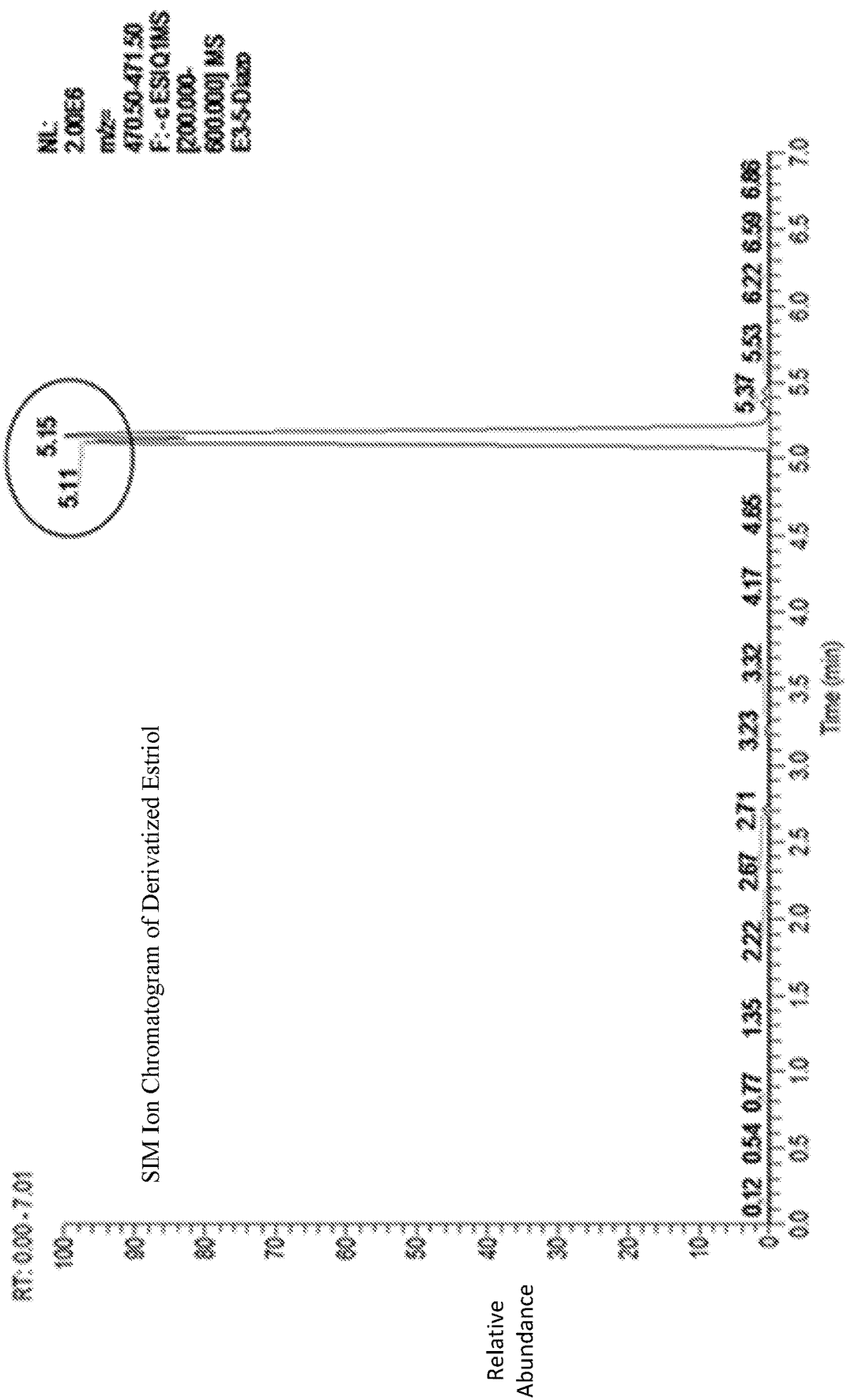
FIG. 8 shows a SIM ion chromatogram of p-sulfanilic acid diazonium-derivatized estriol in Example 3, in accordance with some embodiments.
Figure 9:
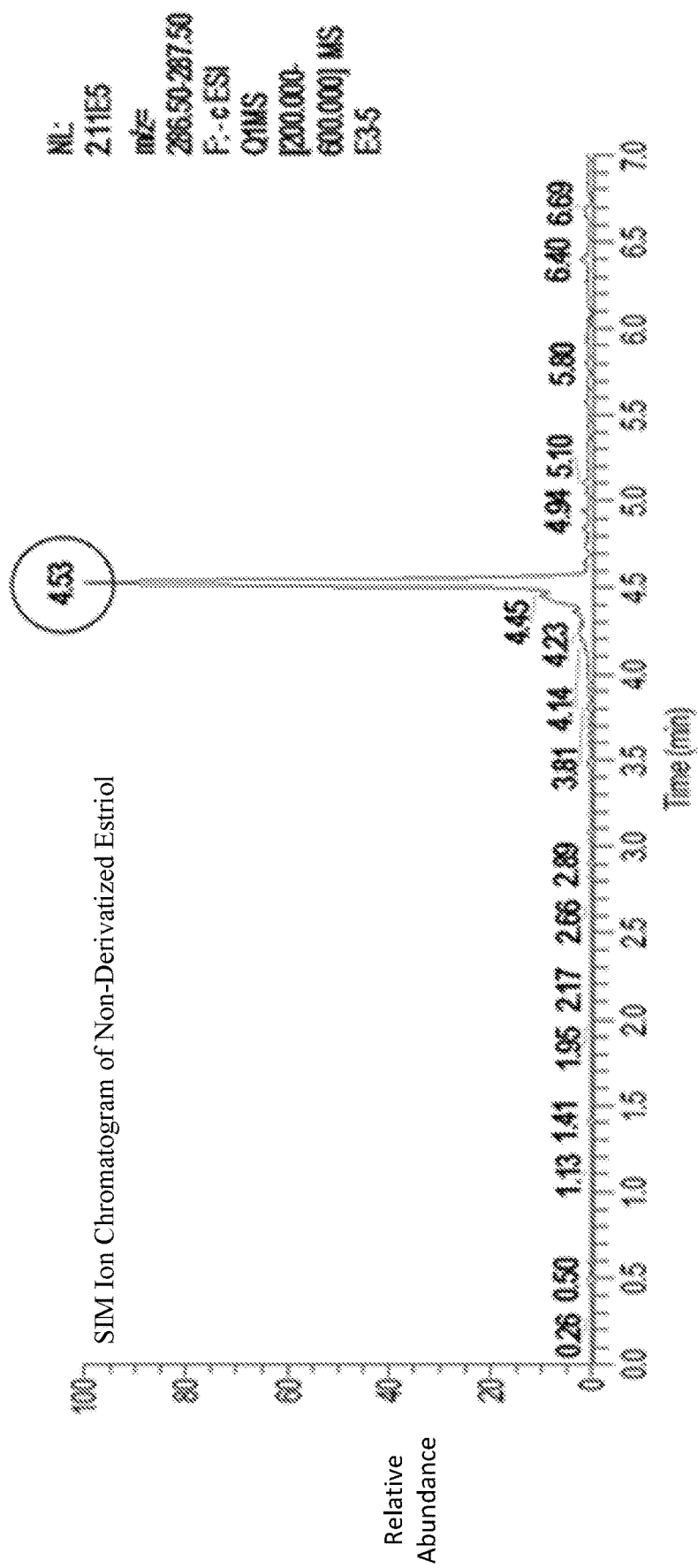
FIG. 9 shows a SIM ion chromatogram of native estriol in Example 3, in accordance with some embodiments.

Referring to FIG. 6, FIG. 8, in negative-ion mode, full-scan mass spectrum is first used to identify the azo derivative of estriol (e.g., circled peak signal in FIG. 6) in the derivatized estriol sample, and then single ion monitoring (SIM) is used to measure its LC-MS signal (e.g., circled peak signal in FIG. 8) in a quantitative manner. Referring to FIG. 7, FIG. 9, in negative-ion mode, full-scan mass spectrum is first used to identify estriol (e.g., circled peak signal in FIG. 7) in the native estriol sample, and then single ion monitoring (SIM) is used to quantitatively measure its LC-MS signal (internal standard-free quantitative analysis) (e.g., circuled peak signal in FIG. 9). By comparison, the LC-MS signal of the azo derivative of estriol (e.g., in FIG. 8) is significantly higher than that of estriol (e.g., in FIG. 9).

Example 4

Comparison of LC-MS Signals of Derivatized Analytes and Native Analytes

LC-MS analysis is implemented on derivatized and native estradiol and estriol samples. Estradiol samples are derivatized using the protocol described in Example 2. Estriol samples are derivatized using the protocol described in Example 3. The analyte concentrations in both sample series are 1.0 µg/ml, 5.0 µg/ml, 10 µg/ml. LC-MS analysis of the samples (internal standard-free quantitative analysis) is carried out in negative-ion mode using single ion monitoring (SIM). LC-MS signals (peak areas) in derivatized samples is compared with those in native samples, as shown in Table 1. The ratio of peak areas in a derivatized sample and the corresponding native sample is calculated to quantify the amplitude of LC-MS signal enhancement.

TABLE 1

Comparison of LC-MS signal of analytes in derivatized samples and that in native samples

| Analyte | Concentration (µg/ml) | Analyte Peak Area in Derivatized Sample (2-Fold Diluted) | Analyte Peak Area in Native Sample | Ratio of Peak Areas (LC-MS Signal Enhancement) |
|---|---|---|---|---|
| Estradiol | 1.0 | 533730 | 23480 | 45.5 |
| | 5.0 | 4722451 | 154045 | 61.3 |
| | 10 | 2845744 | 913169 | 6.2 |

TABLE 1-continued

Comparison of LC-MS signal of analytes in derivatized samples and that in native samples

| Analyte | Concentration (µg/ml) | Analyte Peak Area in Derivatized Sample (2-Fold Diluted) | Analyte Peak Area in Native Sample | Ratio of Peak Areas (LC-MS Signal Enhancement) |
|---|---|---|---|---|
| Estriol | 1.0 | 7825428 | 64230 | 243.7 |
| | 5.0 | 11655912 | 642621 | 36.3 |
| | 10 | 15307553 | 1814941 | 16.9 |

It is found that the peak areas in derivatized estradiol and estriol samples are several to hundreds of times higher than those in native estradiol and estriol samples. The LC-MS conditions for derivatized and native analytes are optimized respectively to the optimal performance of LC-MS analysis. As a conclusion, sensitivity in LC-MS analysis for estradiol and estriol samples may be enhanced a few orders of magnitude through the derivatization method. Thus, derivatization of analytes using a diazonium reagent may be more generally applied to detection and measurement of other aromatic compounds to enhance sensitivity in orders-of-magnitude in LC-MS analysis.

Example 5

Quench of Unreacted Diazonium Reagent

Figure 10:
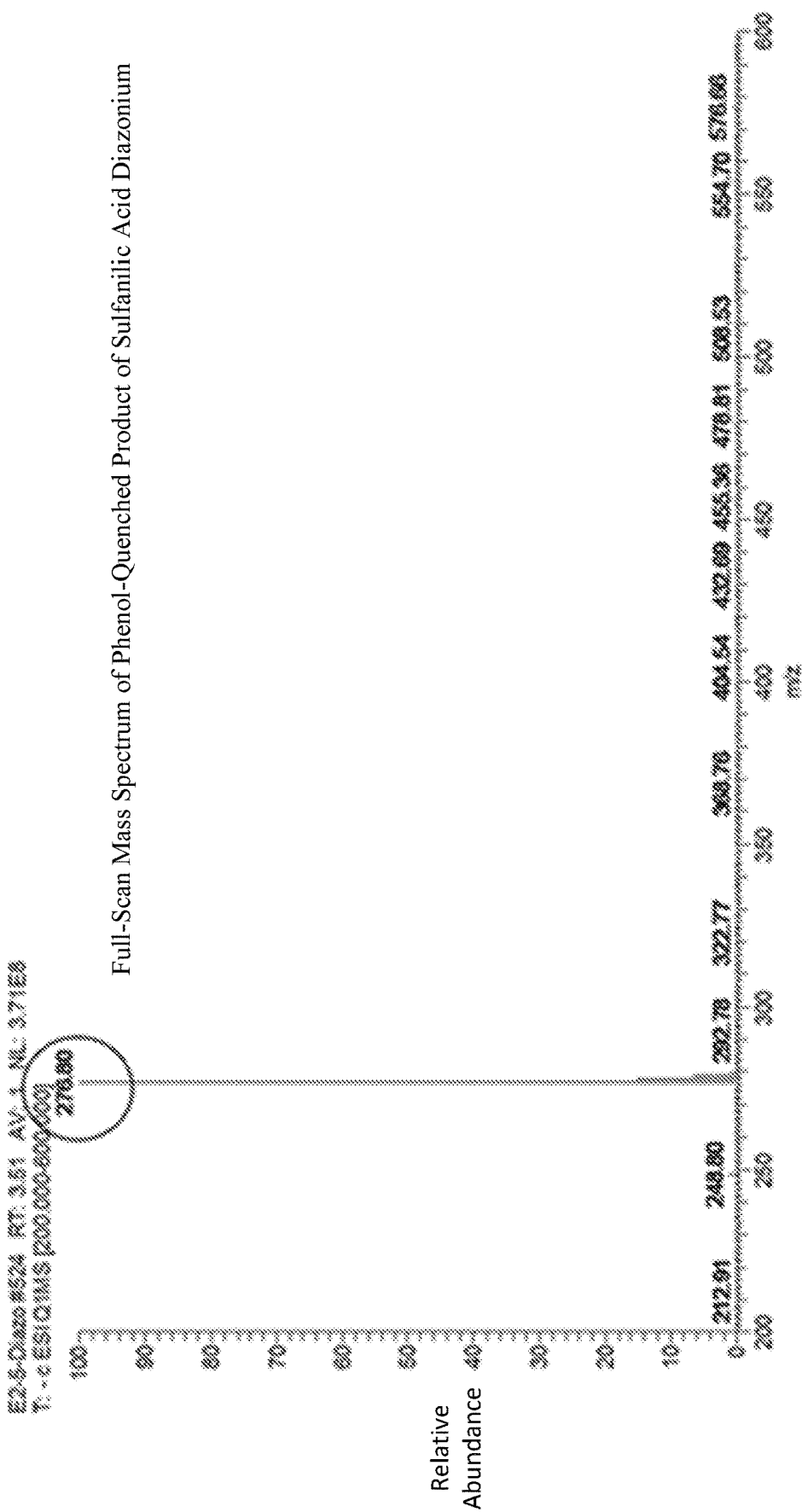
FIG. 10 shows a full-scan mass spectrum of phenol-quenching product of sulfanilic acid diazonium in Example 5, in accordance with some embodiments.
Figure 11:
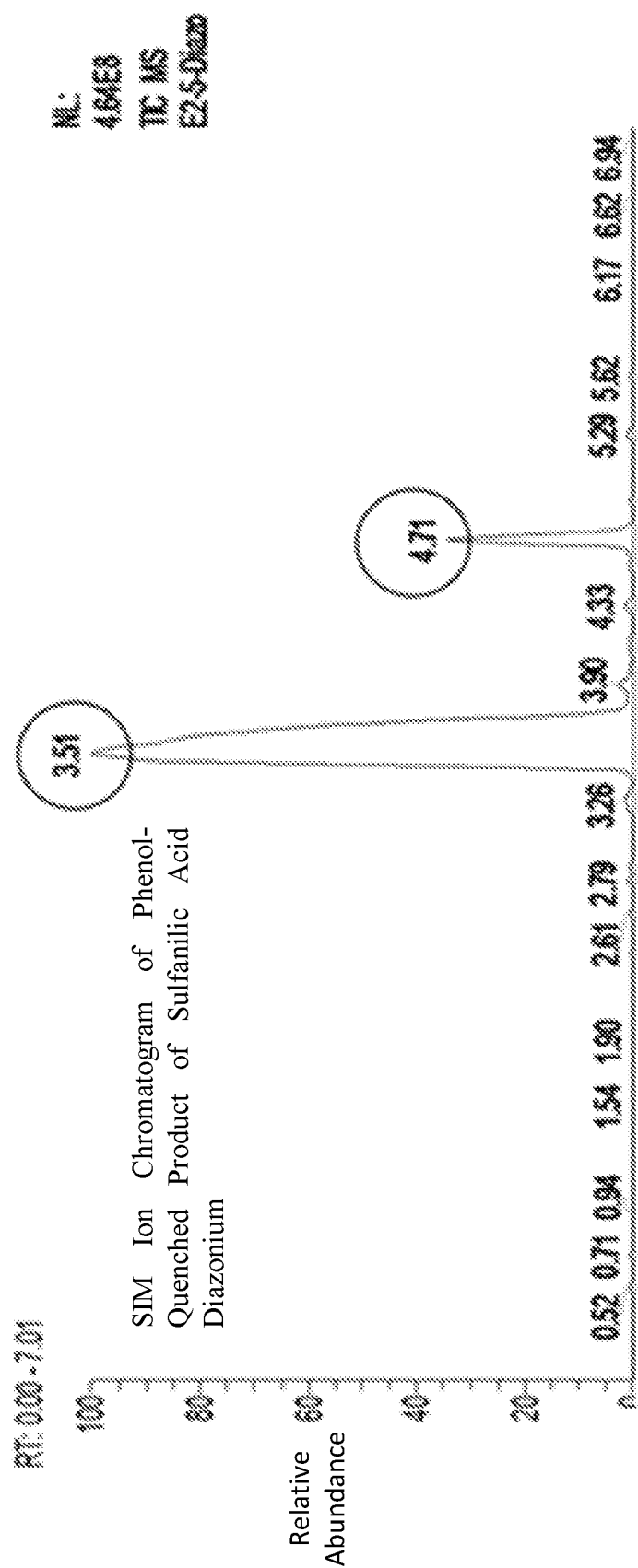
FIG. 11 shows a SIM ion chromatogram of phenol-quenching product of sulfanilic acid diazonium in Example 5, in accordance with some embodiments.

S400, quench the unreacted p-sulfanilic acid diazonium salt after the derivatization of an estradiol sample by adding phenol in the reaction mixture. After quenching the unreacted p-sulfanilic acid diazonium salt in derivatization using phenol, the phenol-quenching product is identified by mass peak in full-scan mass spectrum (FIG. 10) and chromatographic peak in single ion monitoring (SIM) ion chromatogram (FIG. 11). The two chromatographic peaks (e.g., in FIG. 11) denote the two regio-isomers of the quenching product, the ortho- and para-azo derivatives of phenol. When applying the derivatization-based analytical method, the quenching product is optionally diverted away from mass spectrometer by a flowpath switch based on its chromatographic elution time, eliminating its effect to LC-MS analysis of the target analytes.

Example 6

Internal Standard-Added Quantitative Analysis

A mixed standard sample of known concentration of estradiol and estriol is made, and then diluted in 2-fold series to establish a set of 12 standard samples in a concentration range of 0.49 ng/ml~1000 ng/ml. Methanol is used as a control sample.

Internal standard estradiol-13C3 and estriol-13C3 are added into the standard samples. The standard samples are derivatized and analyzed in LC-MS. Multiple reaction monitoring (MRM) scan mode is employed in LC-MS analysis for higher sensitivity than single-ion monitoring (SIM). The azo derivatives of estradiol and estriol are targets of detection, and the azo derivatives of estradiol-13C3 and estriol-13C3 are used as internal standards to correct for analyte loss during sample preparation and variation of ionization efficiency in LC-MS analysis.

Figure 12:
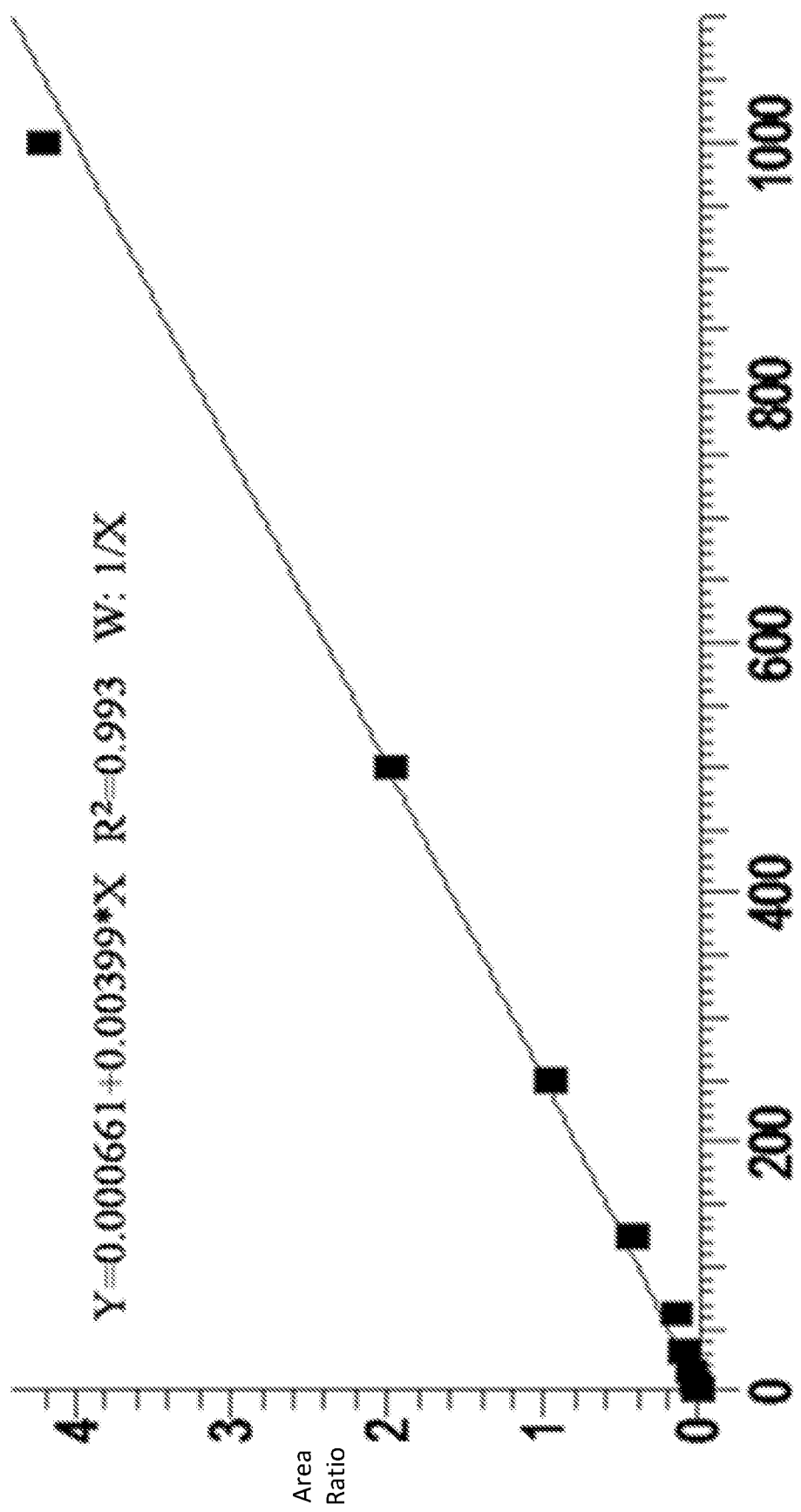
FIG. 12 shows a standard curve of p-sulfanilic acid diazonium-derivatized estradiol for quantitative analysis in Example 6, in accordance with some embodiments.
Figure 13:
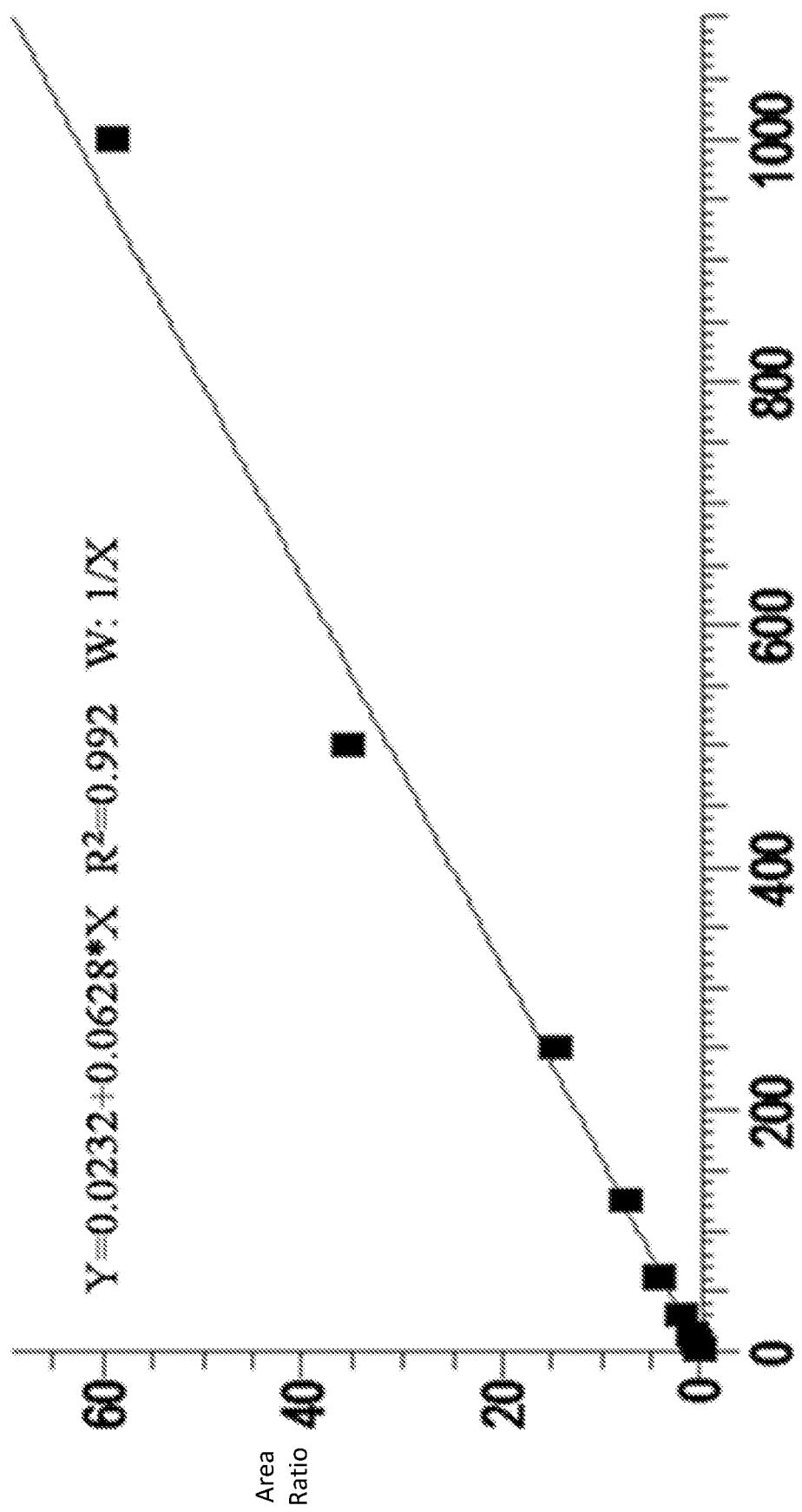
FIG. 13 shows a standard curve of p-sulfanilic acid diazonium-derivatized estriol for quantitative analysis in Example 6, in accordance with some embodiments.

The LC-MS signals on the y-axis are plotted against the analyte concentrations on the x-axis. The plot is fitted using 1/x weighted least squares linear regression. Referring to FIG. 12, FIG. 13, the linearity of the plot is excellent (R2 >0.99) for both estradiol estriol samples in the analyte concentration range of 0.49 ng/ml~1000 ng/ml (along the horizontal axis of the plot).

Linear Equation for Estradiol Samples (FIG. 12): Y=**0.000661+0.00399\*X**; R2=0.993

Linear Equation for Estriol Samples (FIG. 13): Y=**0.0232+0.0628\*X**; R2=0.992

Thus, the derivatization-based analytical method reported in this disclosure is optionally applied to the quantitative analysis of small-volume blood (1 µl~10 µl blood) or dried blood spot (DBS) samples, as well as saliva samples, in various embodiments. The diazonium reagent may be added in excess in the reaction mixture to ensure that the diazonium reagent is not depleted during the derivatization, in some embodiments.

Example 7

Derivatization of Multiple Aromatic Compounds Using Different Derivatization Reagents and the Corresponding LC-MS Analysis Example 7-1-1

N,N-Dimethylaniline+p-Sulfanilic Acid Diazonium Salt (1) Dissolve N,N-dimethylaniline in methanol to make 1.0 µg/ml N,N-dimethylaniline solution.

(2) Mix 21 mg p-sulfanilic acid powder and 8.0 mg sodium nitrite powder, and add 5.0 ml 0.10 mM HCl solution to prepare p-sulfanilic acid diazonium salt solution.

(3) Take 800 µl N,N-dimethylaniline solution, add in 180 µl 5.0 mM ammonium acetate buffer and 20 µl p-sulfanilic acid diazonium salt solution, and incubate at room temperature for 0.5 hr. This step is to derivatize N,N-dimethylaniline and results in a derivatized N,N-dimethylaniline sample.

Example 7-1-2

N,N-Dimethylaniline+Fast Red RC Diazonium Salt (1) Dissolve N,N-dimethylaniline in methanol to make 1.0 µg/mL N,N-dimethylaniline solution.

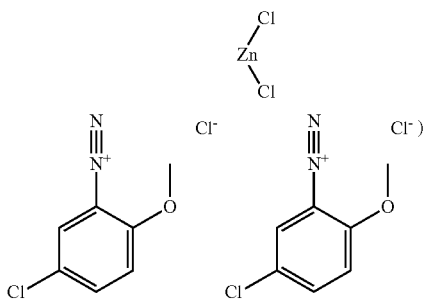

(2) Dissolve Fast Red RC diazonium salt (chemical structure in 5.0 mM ammonium acetate buffer or pH 7.4 phosphate buffer to prepare 1.5 mM Fast Red RC diazonium salt solution.

(3) Take 800 µl N,N-dimethylaniline solution, add in 200 µl Fast Red RC diazonium salt solution, and incubate at room temperature for 0.5 hr. This step is to derivatize N,N-dimethylaniline and results in a derivatized N,N-dimethylaniline sample.

Example 7-1-3

N,N-Dimethylaniline+Fast Red TR Diazonium Salt (1) Dissolve N,N-dimethylaniline in methanol to make 1.0 μg/ml N,N-dimethylaniline solution.
(2) Dissolve Fast Red TR diazonium salt (chemical structure

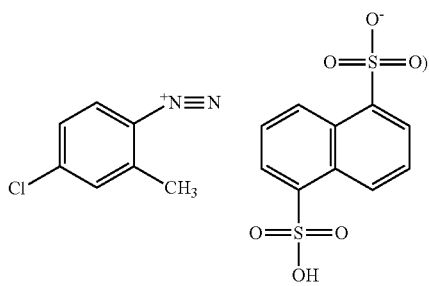

in 5.0 mM ammonium acetate buffer or pH 7.4 phosphate buffer to prepare 1.5 mM Fast Red TR diazonium salt solution.
(3) Take 800 μl N,N-dimethylaniline solution, add in 200 μl Fast Red TR diazonium salt solution, and incubate at room temperature for 0.5 hr. This step is to derivatize N,N-dimethylaniline and results in a derivatized N,N-dimethylaniline sample.

Example 7-2-1

1-Naphthol+p-Sulfanilic Acid Diazonium Salt

The experiment steps are the same as Example 7-1-1 except for replacing N,N-dimethylaniline with 1-naphthol.

Example 7-2-2

1-Naphthol+Fast Red RC Diazonium Salt

The experiment steps are the same as Example 7-1-2 except for replacing N,N-dimethylaniline with 1-naphthol.

Example 7-3-1

Phenol+p-Sulfanilic Acid Diazonium Salt

The experiment steps are the same as Example 7-1-1 except for replacing N,N-dimethylaniline with phenol.

Example 7-3-2

Phenol+Fast Red RC Diazonium Salt

The experiment steps are the same as Example 7-1-2 except for replacing N,N-dimethylaniline with phenol.

Example 7-3-3

Phenol+Fast Red TR Diazonium Salt

The experiment steps are the same as Example 7-1-3 except for replacing N,N-dimethylaniline with phenol.

Example 7-4-2

Estradiol+Fast Red RC Diazonium Salt

The experiment steps are the same as Example 7-1-2 except for replacing N,N-dimethylaniline with estradiol.

Example 7-4-3

Phenol+Fast Red TR Diazonium Salt

The experiment steps are the same as Example 7-1-3 except for replacing N,N-dimethylaniline with estradiol.

Example 7-5-2

Estriol+Fast Red RC Diazonium Salt

The experiment steps are the same as Example 7-1-2 except for replacing N,N-dimethylaniline with estriol.

Example 7-5-3

Estriol+Fast Red TR Diazonium Salt

The experiment steps are the same as Example 7-1-3 except for replacing N,N-dimethylaniline with estriol.

Comparison Example 7-1

Mix 800 μl N,N-dimethylaniline solution and 200 μl 5.0 mM ammonium acetate buffer to prepare a native N,N-dimethylaniline sample.

Comparison Example 7-2

Mix 800 μl 1-naphthol solution and 200 μl 5.0 mM ammonium acetate buffer to prepare a native 1-naphthol sample.

Comparison Example 7-3

Mix 800 μl phenol solution and 200 μl 5.0 mM ammonium acetate buffer to prepare a native phenol sample.

Comparison Example 7-4

Mix 800 μl estradiol solution and 200 μl 5.0 mM ammonium acetate buffer to prepare a native estradiol sample.

Comparison Example 7-5

Mix 800 μl estriol solution and 200 μl 5.0 mM ammonium acetate buffer to prepare a native estriol sample.

In LC-MS analysis, MS scan types of full-scan, single ion monitoring (SIM), or multiple reaction monitoring (MRM) (also named as selected reaction monitoring) are usually employed. Full-scan is used to view the mass of sample components to identify the target of detection, and SIM or MRM is used for quantitative analysis. Typically, SIM is easier to implement as it does not require optimization of mass transitions of analyte, but using MRM results in higher sensitivity than using SIM in an analytical method due to reduced background noise.

Figure 14:
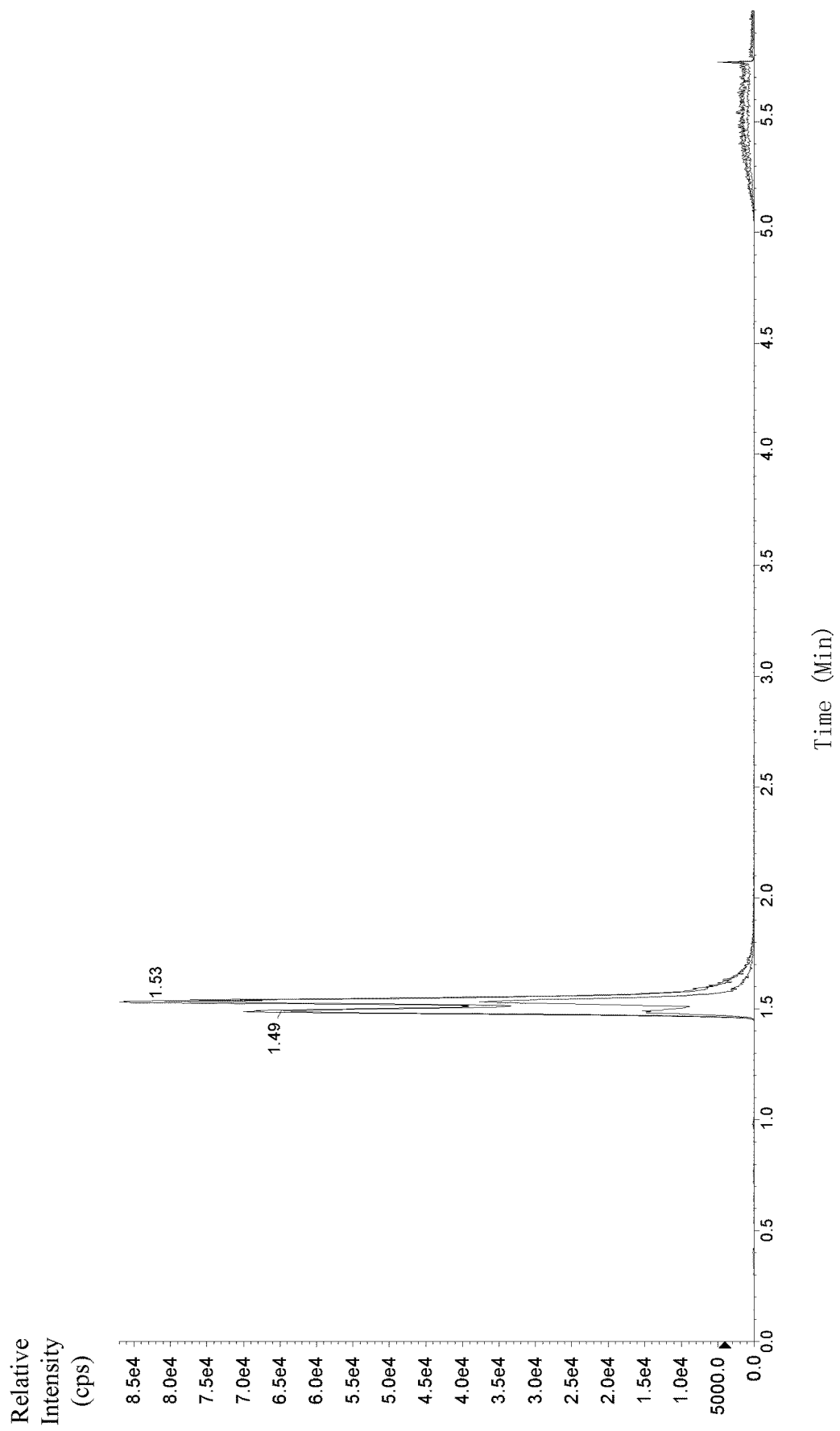
FIG. 14 shows a multiple reaction monitoring (MRM) ion chromatogram of Fast Red RC diazonium-derivatized estradiol in Example 7-4-2, in accordance with some embodiments.
Figure 15:
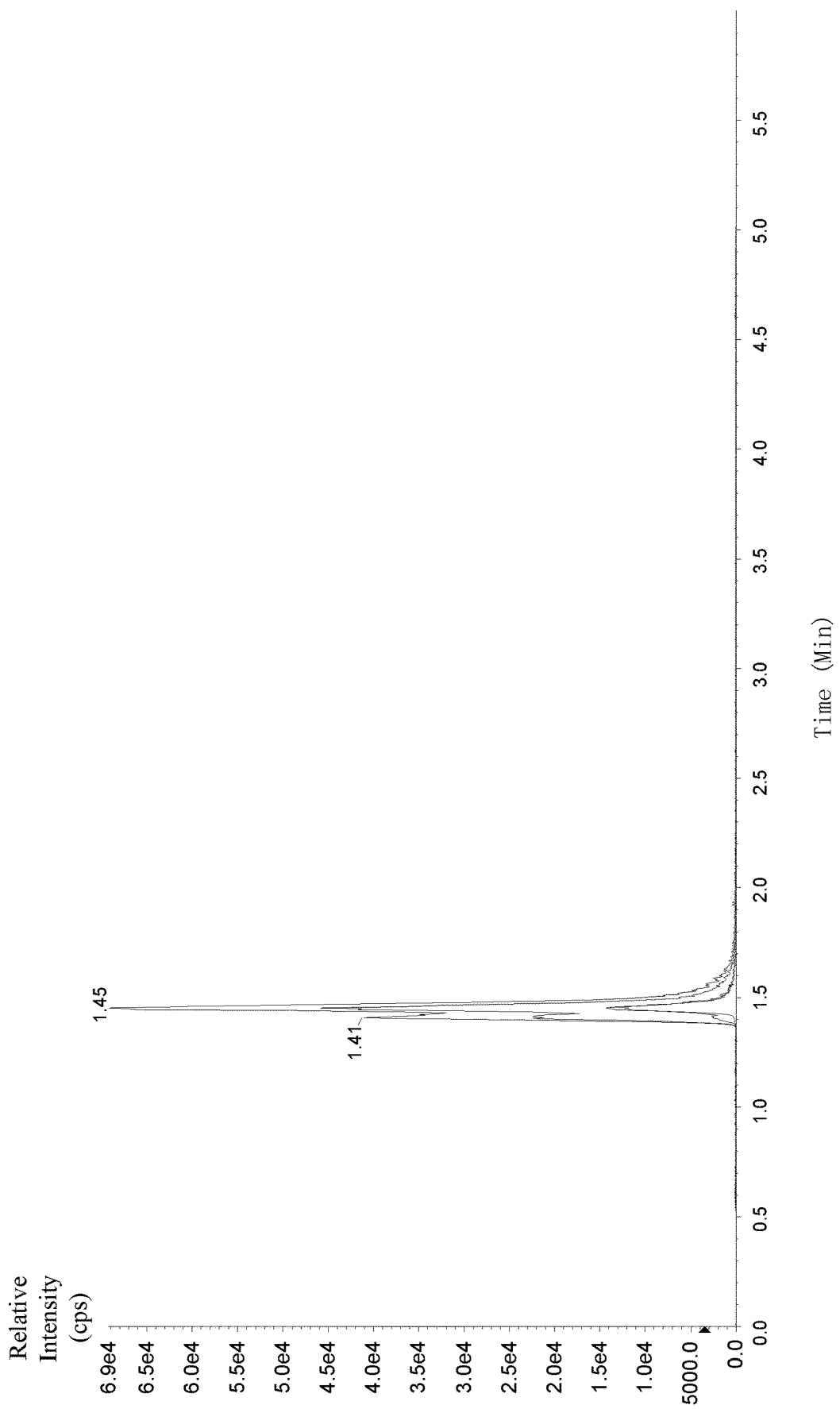
FIG. 15 shows a MRM ion chromatogram of Fast Red TR diazonium-derivatized estradiol in Example 7-4-3, in accordance with some embodiments.
Figure 16:
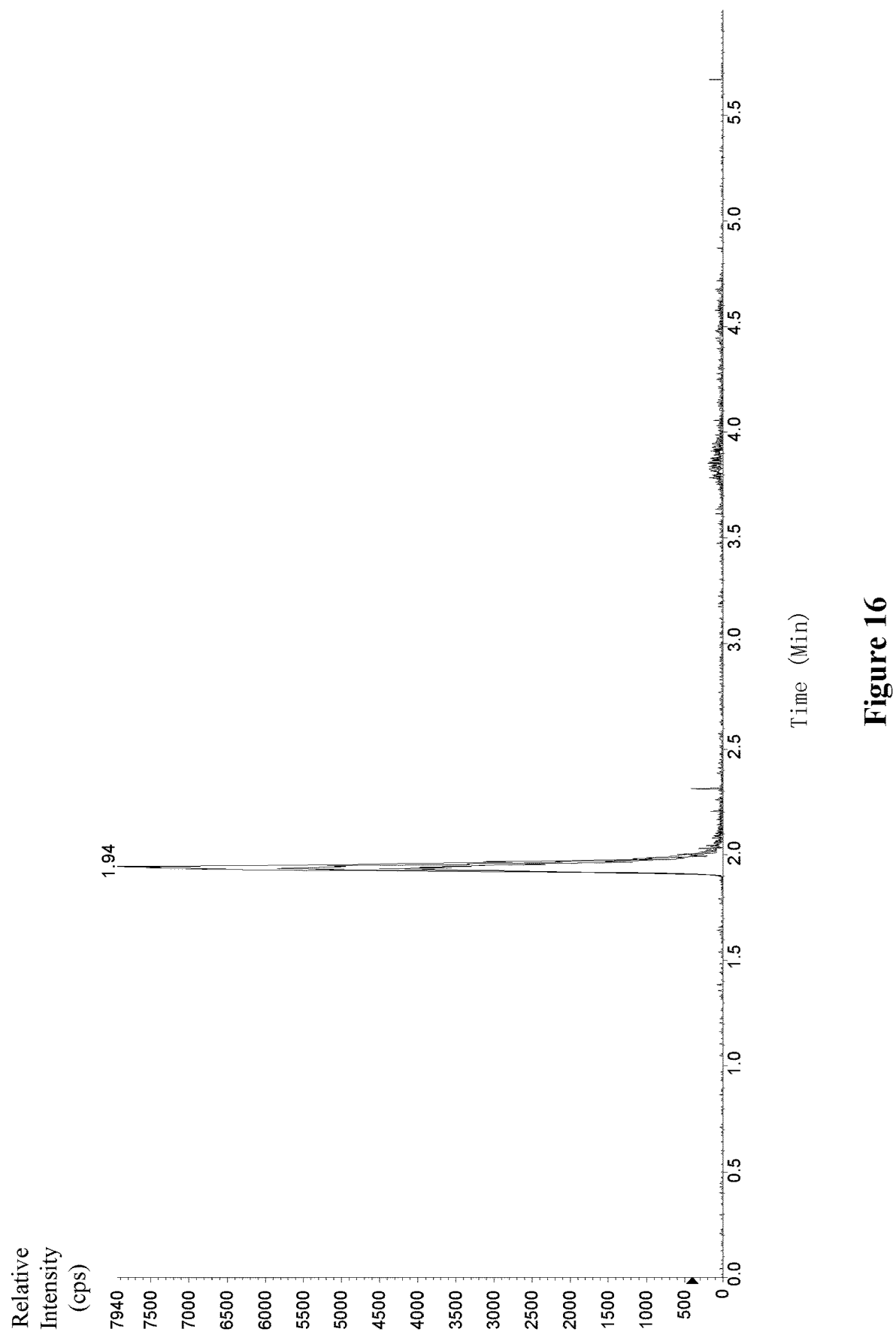
FIG. 16 shows a MRM ion chromatogram of native estradiol in Comparison Example 7-4, in accordance with some embodiments.
Figure 17:
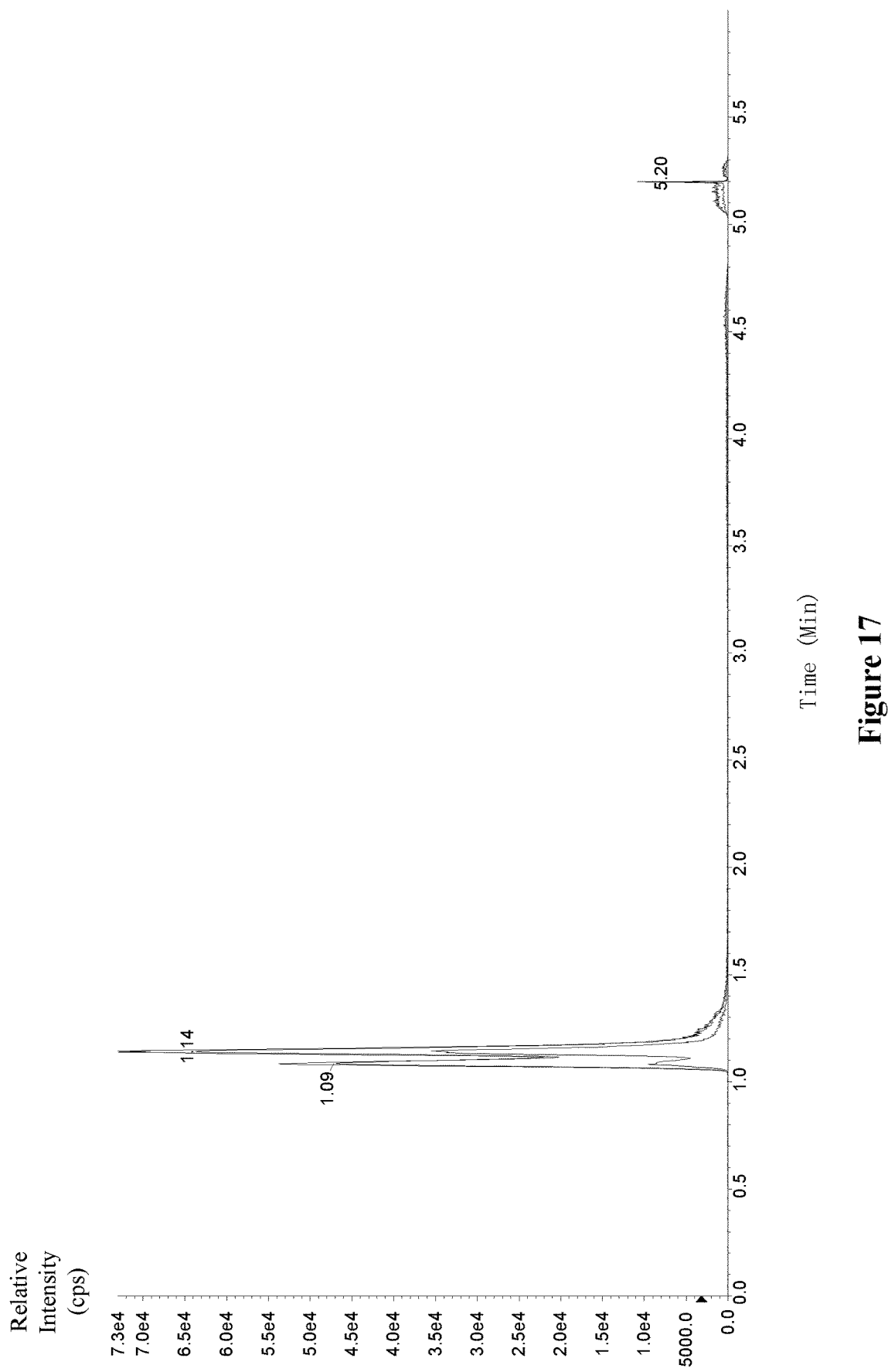
FIG. 17 shows a MRM ion chromatogram of Fast Red RC diazonium-derivatized estriol in Example 7-5-2, in accordance with some embodiments.
Figure 18:
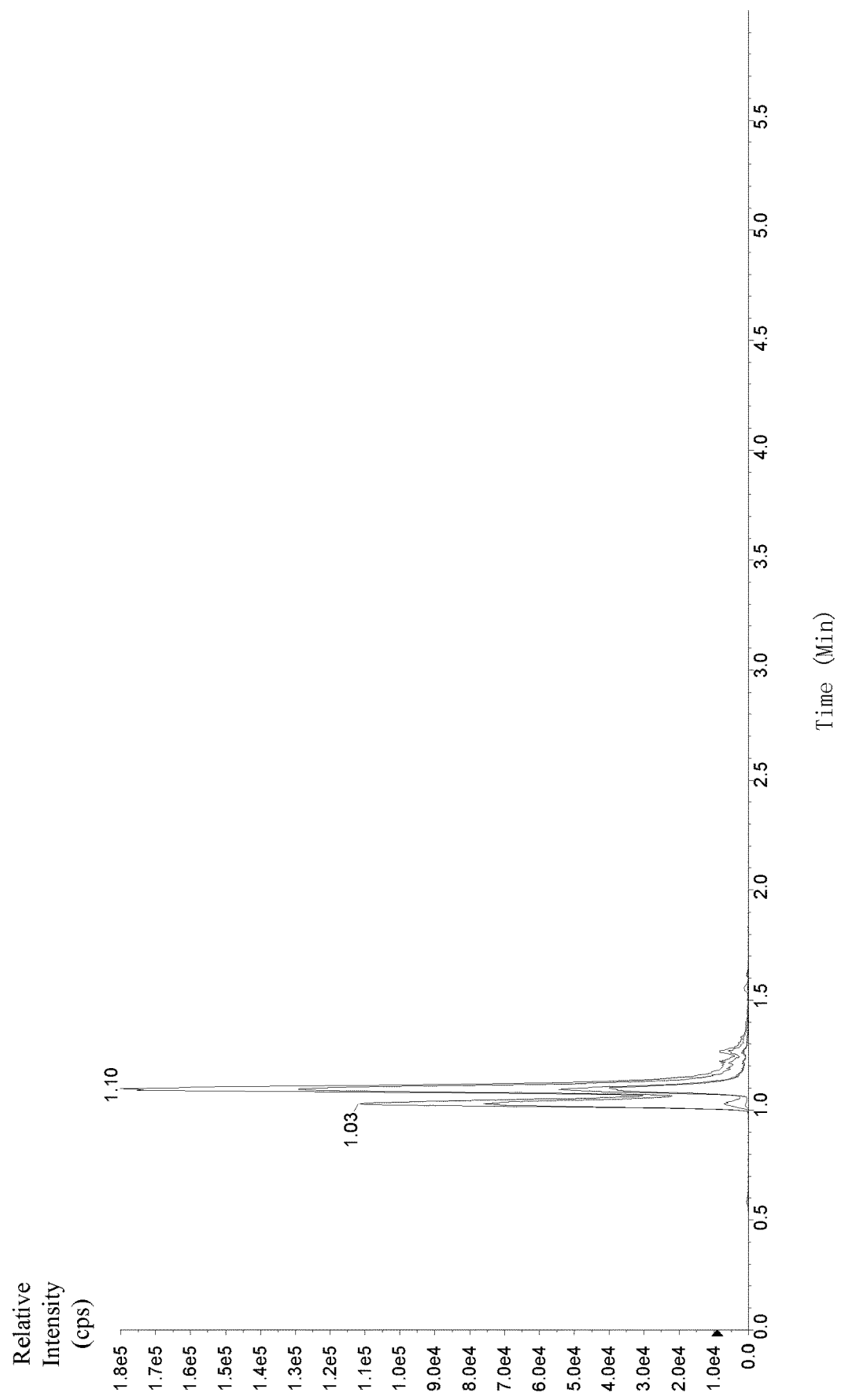
FIG. 18 shows a MRM ion chromatogram of Fast Red TR diazonium-derivatized estriol in Example 7-5-3, in accordance with some embodiments.
Figure 19:
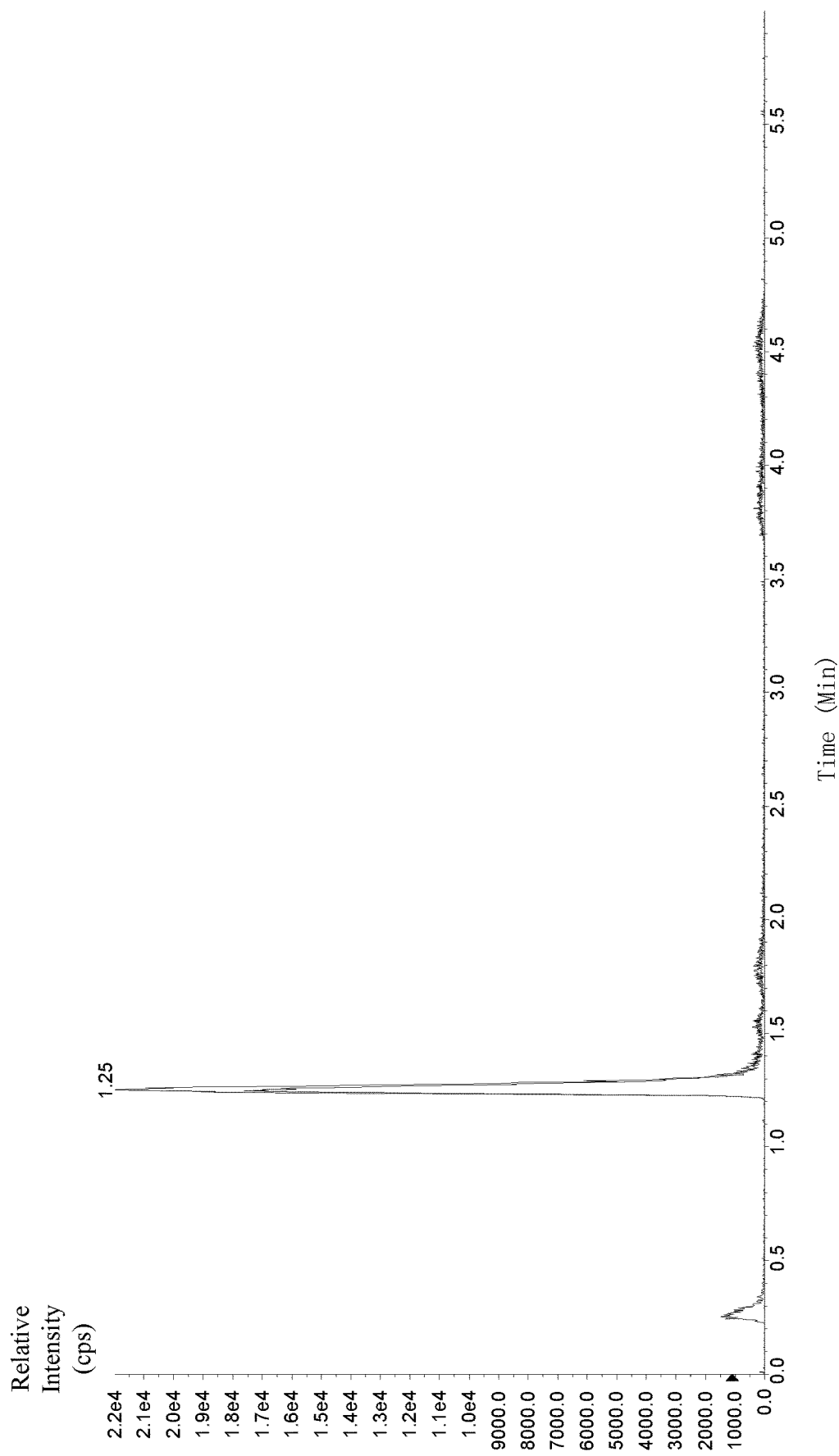
FIG. 19 shows a MRM ion chromatogram of native estriol in Comparison Example 7-5, in accordance with some embodiments.

The LC-MS analysis of the samples in Example 7 is carried out in MRM scan type, and the LC-MS conditions are optimized for each analyte respectively. Referring to FIG. 14 FIG. 19, in the MRM ion chromatograms of native and derivatized estradiol and estriol samples, the LC-MS signals (peak areas) of derivatized samples are significantly higher than those of native samples. In addition, it is observed that the MRM ion chromatograms have lower background noise and higher sensitivity and specificity than the SIM ion chromatograms (see for example FIGS. 4, 5, 8, 9).

To illustrate the LC-MS signal enhancement resulted from the derivatization method, Table 2 displays the peak area in MRM ion chromatogram for each analyte in both derivatized and native samples, and the ratio of the corresponding peak areas. Because the LC-MS analysis of p-sulfanilic acid diazonium-derivatized estradiol and estriol was carried out in Example 3, the experiment is not repeated in Example 7. Based on the results in Table 2, in contrast to the native samples in Comparison Examples 7-1~7-5, the LC-MS signals of the corresponding derivatized samples in Examples 7-1-1~7-5-3 are all enhanced, which proves that the azo coupling-based derivatization method has broad applicability to aromatic compounds.

(3) Take 800 µl N,N-dimethylaniline solution, add in 200 µl Fast Red RC diazonium salt solution, and incubate at room temperature for 0.5 hr. This step is to derivatize THC and results in a derivatized THC sample.

Example 8-1-2

THC+Fast Red TR Diazonium Salt (1) Dissolve THC in methanol to make 1.0 µg/ml THC solution.
(2) Dissolve Fast Red TR diazonium salt in 5.0 mM ammonium acetate buffer or pH 7.4 phosphate buffer to prepare 1.5 mM Fast Red TR diazonium salt solution.
(3) Take 800 µl THC solution, add in 200 µl Fast Red TR diazonium salt solution, and incubate at room temperature for 0.5 hr. This step is to derivatize THC and results in a derivatized THC sample.

Example 8-2-1

THCCOOH+Fast Red RC Diazonium Salt

The experiment steps are the same as Example 8-1-1 except for replacing THC with THCCOOH.

TABLE 2

Comparison of LC-MS signal of analytes in derivatized samples and that in native samples (multiple diazonium reagents and different analytes)

| | Native | | p-Sulfanilic Acid Diazonium Derivative | | | Fast Red RC Derivative | | | Fast Red TR Derivative | | |
|---|---|---|---|---|---|---|---|---|---|---|---|
| | | | | | Ratio of | | | Ratio of | | | Ratio of |
| Compound | Mode | Peak Area | Mode | Peak Area | Peak Areas | Mode | Peak Area | Peak Areas | Mode | Peak Area | Peak Areas |
| Dimethyl-aniline | Positive Ion | 9.06E+04 | Nagative Ion | 1.25E+05 | 1.4 | Positive Ion | 8.01E+05 | 8.8 | Positive Ion | 8.01E+05 | 8.8 |
| Naphthol | Nagative Ion | 5.43E+05 | Nagative Ion | 6.61E+05 | 1.2 | Positive Ion | 1.00E+06 | 1.8 | Positive Ion | / | / |
| Phenol | Nagative Ion | Undetectable | Nagative Ion | 1.80E+06 | / | Positive Ion | 1.21E+05 | / | Positive Ion | 1.30E+05 | / |
| Estradiol | Nagative Ion | 1.88E+04 | / | / | / | Positive Ion | 3.13E+05 | 16.6 | Positive Ion | 2.81E+05 | 14.9 |
| Estriol | Nagative Ion | 6.21E+04 | / | / | / | Positive Ion | 1.82E+05 | 2.9 | Positive Ion | 4.91E+05 | 7.9 |

Note:
Numbers in Table 2 are presented in scientific notation.

Example 8

Derivatization of Multiple Cannabinoids Using Different Derivatization Reagents and the Corresponding LC-MS Analysis (THC—Δ9-Tetrahydrocannabinol; 11-OH-THC-11-Hydroxy-Δ9-Tetrahydrocannabinol; HCCOOH—11-Nor-9-Δ9-Carboxy-Tetrahydrocannabinol; CBD—Cannabidiol; CBN—Cannabinol)

Example 8-1-1

THC+Fast Red RC Diazonium Salt (1) Dissolve THC in methanol to make 1.0 µg/ml THC solution.
(2) Dissolve Fast Red RC diazonium salt in 5.0 mM ammonium acetate buffer or pH 7.4 phosphate buffer to prepare 1.5 mM Fast Red RC diazonium salt solution.

Example 8-2-2

THCCOOH+Fast Red TR Diazonium Salt

The experiment steps are the same as Example 8-1-2 except for replacing THC with THCCOOH.

Example 8-3-1

11-OH-THC+Fast Red RC Diazonium Salt

The experiment steps are the same as Example 8-1-1 except for replacing THC with 11-OH-THC.

Example 8-3-2

11-OH-THC+Fast Red TR Diazonium Salt

The experiment steps are the same as Example 8-1-2 except for replacing THC with 11-OH-THC.

Example 8-4-1

CBD+Fast Red RC Diazonium Salt

The experiment steps are the same as Example 8-1-1 except for replacing THC with CBD.

Example 8-4-2

CBD+Fast Red TR Diazonium Salt

The experiment steps are the same as Example 8-1-2 except for replacing THC with CBD.

Example 8-5-1

CBN+Fast Red RC Diazonium Salt

The experiment steps are the same as Example 8-1-1 except for replacing THC with CBN.

Example 8-5-2

CBN+Fast Red TR Diazonium Salt

The experiment steps are the same as Example 8-1-2 except for replacing THC with CBN.

Comparison Example 8-1

Mix 800 μl THC solution and 200 μl 5.0 mM ammonium acetate buffer to prepare a native THC sample.

Comparison Example 8-2

Mix 800 μl 11-OH-THC solution and 200 μl 5.0 mM ammonium acetate buffer to prepare a native 11-OH-THC sample.

Comparison Example 8-3

Mix 800 μl THCCOOH solution and 200 μl 5.0 mM ammonium acetate buffer to prepare a native THCCOOH sample.

Comparison Example 8-4

Mix 800 μl CBD solution and 200 μl 5.0 mM ammonium acetate buffer to prepare a native CBD sample.

Comparison Example 8-5

Mix 800 μl CBN solution and 200 μl 5.0 mM ammonium acetate buffer to prepare a native CBN sample.

The LC-MS analysis of the samples in Example 8 is carried out in MRM scan type. Negative-ion mode is to be used for native analytes (for THC it can be either positive-ion mode or negative-ion mode), and positive-ion mode is to be used for derivatized analytes, in some embodiments. It is recommended to use full-scan to view the mass of sample components to identify the target of detection, and MRM for quantitative analysis. The LC-MS conditions should be optimized for each analyte respectively. By comparing the LC-MS signals (peak areas) of derivatized analytes and those of native samples in the MRM ion chromatograms, it can be shown that the amplitude of LC-MS signal enhancement is from several times to several hundreds of times through the derivatization of analytes.

The examples above only illustrate a few applications of this invention, of which the descriptions are specific and detailed, but they should not be considered as restrictions to the range of this invention. It should be noted that for normal technicians in this field, it is possible to make alternatives and improvements, which are all within the protection range of this patent application. Therefore, the protection range of this patent application should be in accordance with the claims.

What is claimed is:

1. A method of analyzing aromatic compounds in a sample, comprising:
   preparing a diazonium reagent;
   contacting the aromatic compounds in the sample with the diazonium reagent to form a first analyte;
   measuring an amount or ratio of the first analyte to the sample that has been formed by liquid chromatography-mass spectrometry analyzing; and
   extrapolating presence or quantity of the aromatic compounds in the sample based on the measured amount or ratio of the first analyte to the sample that has been formed;
   wherein the contacting comprises having azo coupling reaction between the diazonium reagent and the aromatic compounds, and the analyte is an azo-coupled analyte;
   wherein the diazonium reagent contains one or more functional groups that are negatively or positively charged during liquid chromatography-mass spectrometry analyzing; the functional groups that are negatively charged in the diazonium reagent comprise one or more of sulfonate group ($-SO_3^-$), carboxylate group ($-COO^-$), sulfonic acid group ($-SO_3H$) and carboxylic acid group ($-COOH$), and the functional groups that are positively charged in the diazonium reagent include one or more of quaternary ammonium group, amino group and thiol group;
   wherein the diazonium reagent is p-sulfanilic acid diazonium salt solution, Fast Red RC Diazonium Salt or Fast Red TR Diazonium Salt;
   when the diazonium reagent is p-sulfanilic acid diazonium salt solution, the aromatic compounds in the sample is Estriol or Estradiol; and
   when the diazonium reagent is Fast Red RC Diazonium Salt or Fast Red TR Diazonium Salt, the aromatic compounds in the sample is cannabidiol compounds, Estriol or Estradiol.

2. The method of claim 1, wherein the diazonium reagent is prepared by a diazotization reaction of an amine and nitrous acid, and materials to prepare the diazonium reagent comprise an amine, a solvent, nitrous acid or materials to prepare the nitrous acid.

3. The method of claim 2, wherein the nitrous acid is prepared from precursor materials on site, and the nitrous acid then reacts with amine to prepare the diazonium reagent immediately prior to the liquid chromatography-mass spectrometry analyzing, wherein the precursor materials comprise a nitrite and an acid.

4. The method of claim 2, wherein the solvent to prepare the diazonium reagent comprises sodium hydroxide solution or sodium bicarbonate solution, which dissolve an amino group-contained acid, to prevent precipitation of inner salt formed in acidic an environment.

5. The method of claim 2, wherein when the diazonium reagent is p-sulfanilic acid diazonium salt solution, the diazonium reagent is prepared by: measuring p-sulfanilic acid powder and dissolving it in sodium hydroxide solution to form a mixture; and adding sodium nitrite powder and HCl solution to the mixture.

6. The method of claim 2, wherein when the diazonium reagent is Fast Red RC Diazonium Salt or Fast Red TR Diazonium Salt, the diazonium reagent is prepared by: dissolving Fast Red RC diazonium salt or Fast Red TR diazonium salt in pH 7.4 phosphate buffer.

7. The method of claim 1, further comprising adding a quencher to the sample after the contacting to quench unreacted diazonium reagent by reacting with—$N^{2+}$, wherein the quencher is an aromatic compound containing one or more electron-donating groups.

8. The method of claim 7, wherein the quencher includes one or more of ascorbic acid, organic halides, and aliphatic compounds with active methylene groups.

9. The method of claim 7, wherein the quencher includes one or more of phenol, phenol derivatives, naphthol, naphthol derivatives, and aniline derivatives.

10. The method of claim 9, wherein the quencher is phenol.

11. The method of claim 1, wherein the sample contains water, and the sample is directly modified with the diazonium reagent without having to first dry the water-containing sample.

12. The method of claim 1 wherein, the diazonium reagent is p-sulfanilic acid diazonium salt solution.

13. The method of claim 1 wherein, the diazonium reagent is Fast Red RC Diazonium Salt or Fast Red TR Diazonium Salt.

\* \* \* \* \*